(12) United States Patent
Tang et al.

(10) Patent No.: US 6,566,104 B1
(45) Date of Patent: May 20, 2003

(54) ERBB-4 TARGETED RIBOZYMES

(75) Inventors: Careen K. Tang, Bethesda, MD (US); Marc E. Lippman, Ann Arbor, MI (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/530,224

(22) PCT Filed: Oct. 30, 1998

(86) PCT No.: PCT/US98/23279

§ 371 (c)(1),
(2), (4) Date: Jun. 23, 2000

(87) PCT Pub. No.: WO99/23209

PCT Pub. Date: May 14, 1999

(51) Int. Cl.[7] .............................. C12P 19/34; C12Q 1/68; C12N 15/63; C07H 21/02; C07H 21/04
(52) U.S. Cl. .......................... 435/91.31; 435/6; 435/91.1; 435/455; 435/458; 536/23.1; 536/24.5
(58) Field of Search ........................ 435/6, 91.1, 91.31, 435/455, 458, 366, 375; 514/44; 536/23.1, 24.5

(56) References Cited

U.S. PATENT DOCUMENTS 5,811,098 A * 9/1998 Plowman et al. ......... 424/178.1
5,972,704 A * 10/1999 Draper et al. ............... 435/375

OTHER PUBLICATIONS

Natalie Milner et al., Selecting effectinve antisense reagents on combinatorial oligonucleotide arrays, Nature Biotechnology, vol. 15, Jun. 1997, pp. 537–541.*
Stanley T. Crooke, Antisense Research and Application, pp. 1–45.*
Sir William Dunn, Towards gene–inhibition therapy: a review of progress and prospects in the field of antiviral antisense nucleic acids and ribozymes, Antiviral Chemistry & Chemotherapy (1991) 2(4) pp. 191–214.*
Andrea D. Branch, A good antisense molecule is hard to find, TIBS 23—Feb. 1998 pp. 45–50.*
Giorgio Palu' et al., In Pursuit of new developments for gene therapy of human deseases, Journal of Biotechnology 68 (1999) pp. 1–13.*
Karen Pihl–Carey, Isis To Restructure As Crohn's Disease Drug Fails In Phase III, Bioworld Today, vol. 10, No. 239 pp. 1–2.*
Careen K. Tang et al., ErbB–4 Ribozymes Abolish Neuregulin–induced Mitogenesis, Cancer Research 58, pp. 3415–3422, Aug. 1, 1998.*

* cited by examiner

Primary Examiner—Sean McGarry
Assistant Examiner—Jane Zara
(74) Attorney, Agent, or Firm—Pillsbury Winthrop LLP

(57) ABSTRACT

Enzymatic RNA molecules which cleave ErbB-4 mRNA and uses thereof.

2 Claims, 13 Drawing Sheets

SEQUENCE LISTING

<160> NUMBER OF SEQ ID NOS: 8

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: mRNA target
      sequence

<400> SEQUENCE: 1
gacuuugggu cugggugag                                                   19

<210> SEQ ID NO 2
<211> LENGTH: 16
<212> TYPE: RNA
<213> ORGANISM: Artificial Sequence
<220> FEATURE:
<223> OTHER INFORMATION: Description of Artificial Sequence: mRNA target
      sequence

<400> SEQUENCE: 2
ugagguuguc augggc                                                      16

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: mRNA target
      sequence

```
<400> SEQUENCE: 3
gucacaggcu acguguuag                                              19

<210> SEQ ID NO 4
<211> LENGTH: 49
<212> TYPE: RNA
<213> ORGANISM: Artificial Sequence
<220> FEATURE:
<223> OTHER INFORMATION: Description of Artificial Sequence: Synthetic
      ribozyme sequence

<400> SEQUENCE: 4
aauucggcuc acccacugau gaguccguga ggacgaaacc caaaguccc             49

<210> SEQ ID NO 5
<211> LENGTH: 47
<212> TYPE: RNA
<213> ORGANISM: Artificial Sequence
<220> FEATURE:
<223> OTHER INFORMATION: Description of Artificial Sequence: Synthetic
      ribozyme sequence

<400> SEQUENCE: 5 aaucguugc ccaucugaug aguccgugag gacgaaacaa ccucacc                47

<210> SEQ ID NO 6
<211> LENGTH: 49
<212> TYPE: RNA
<213> ORGANISM: Artificial Sequence
<220> FEATURE:
<223> OTHER INFORMATION: Description of Artificial Sequence: Synthetic
      ribozyme sequence

<400> SEQUENCE: 6 aauccacua acacgcugau gaguccguga ggacgaaagc cugugacuc              49

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
aattgtcagc acgggatctg agac                                        24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
gtttccttaa acaagaccag atgt                                        24
```

ERBB-4 TARGETED RIBOZYMES

CROSS-REFERENCE TO RELATED APPLICATIONS

This application claims priority to international application No. PCT/US98/23279 filed Oct. 30, 1998, which in turn claims priority to provisional application No. 60/063,875 filed Oct. 31, 1997.

INTRODUCTION

This invention relates to methods for inhibition of growth of transformed cells, and treatment and diagnosis of diseases and conditions related to ErbB-4 expression.

The epidermal growth factor (EGF) receptors have been implicated in human cancer more frequently than any other family of growth factor receptors. The EGF receptor gene is often amplified or overexpressed in squamous cell carcinoma and glioblastomas [Jenkins et al. (1989) *Cancer Genet. Cytogenet.* 39:253]. Similarly, ErbB-4 is overexpressed in adenocarcinomas of the stomach, breast and ovary.

The epidermal growth factor receptor (EGFR/ErbB) family is a group of tyrosine kinases that is frequently overexpressed in a variety of carcinomas [Gullick, W. J. (1991) *Br. Med. Bull.* 47:87–98; Hynes, N. E. and Stern, D. F. (1994) *Biochem. Biophys. Acta* 1198:165–184; Lemoine, N. R. et al. (1992) *Br. J. Cancer* 66:1116–1121]. This class I subfamily of receptors is comprised of four members: EGFR [Xu, Y. H. et al. (1984) *Nature* 309:806–810], HER2/ErbB-2/neu [Schechter, A. L. et al. (1984) *Nature* 312:513–516], HER3/ErbB-3 [Kraus, M. H. et al. *Proc. Natl. Acad. Sci. USA* 86:9193–9197; Plowman, G. D. et al. (1990) *Proc. Natl. Acad. Sci. USA* 87:4905–4909], and HER4/ErbB-4 [Plowman, G. D. et al. (1993) *Proc. Natl. Acad. Sci. USA* 90:1746–1750]. Data from numerous laboratories suggest that the EGFR family members may play a complex role in signaling [Wada, T. et al. (1990) *Cell* 61:1339–1347; Goldman, R. et al. (1990) *Biochemistry* 29:11024–11028; Caraway, K. L. and Cantley L. C. (1994) *Cell* 78:5–8]. Most human breast cancer cells express more than one of the EGF family receptors, and different combinations of receptors can heterodimerize or homodimerize. These receptor interactions lead to the activation of multiple signaling pathways and contribute to the pathogenicity and tumorigenicity of breast cancer [Earp, S. H. et al. (1995) *Breast Cancer Resarch and Treatment*].

A number of growth factors, classified as EGF-like ligands, have been identified that bind and stimulate the kinase activity of EGF-family receptors. EGF, transforming growth factor α (TGFα), amphiregulin (AR), heparin-binding EGF(HB-EGF), and betacellulin (BTC) have been described as specific for EGFR [Savage, C. R. et al. (1972) *J. Biol. Chem.* 241:7612–7621; Marquardt, H. et al. (1983) *Science* 223:1079–1082; Shoyab, M. et al. (1989) *Science* 243:1079–1082; Higashiyama, S. et al. (1991) *Science* 251: 936–939; shing, Y. et al. (1993) *Science* 259:1604–1607]. Several differentially spliced variants, named heregulin (HRG) also known as neuregulin (NRG), or neu differentiation factor (NDF) [Holmes, W. E. et al. (1992) *Science* 256:1205–1210; Wen, D. et al. (1992) *Cell* 69:559–572], acetylcholine-receptor inducing activity (ARIA) [Falls, D. G. et al. (1993) *Cell* 72:801–815], glial growth factor (GGF) [Marchionni, M. A. et al. (1993) *Nature* (London)362: 312–318] and gp30 [Lupu, R. et al. (1990) *Science* 249:1552–1555], were initially identified as candidate neu ligands by their ability to induce neu tyrosine phosphorylation [Peles, E. and Yarden, Y. (1993) *Bioassays* 15:815–824]. However, recent results demonstrate that ErbB-3 and ErbB-4 are primary receptors for heregulin [Plowman, G. D. et al. (1993) *Nature* 366:473–475; Carraway, K. L. III et al. (1994) *J. Biol. Chem.* 269: 14303–14306]. Activation of ErbB-2 by HRG is thought to occur through transphosphorylation resulting from heterodimerization with either ErbB-3 or ErbB-4 [Tzahar, E. et al. (1994) *J. Biol. Chem.* 269:40:25226–25223; Peles, E. et al. (1993) *EMBO J.* 12:961–971; Sliwkowski, M. X. et al. (1994) *J. Biol. Chem.* 269: 14661–14665]. Most recently, betacellulin was also shown to activate the ErbB-4 receptor in a Ba/F3 system [Riesell, D. J. et al. (1996) *Oncogene* 12: 245–353].

Amplification and/or overexpression of EGFR and ErbB-2 are clearly important factors in neoplastic transformation of breast epithelium [Jardines, L. et al. (1993) *Pathobiology* 61:268–282]. Elevated ErbB-4 levels have been found in certain breast cancer cell lines [Plowman, G. D. et al. (1993) *Proc. Natl. Acad. Sci. USA* 90:1746–1750], but little is known about the expression or the clinical significance of ErbB-4 receptors in the diagnosis and prognosis of human breast cancer.

SUMMARY OF THE INVENTION

To investigate the biological significance of ErbB-4 in human breast cancer, we used molecular targeting of the ErbB-4 mRNA by ribozymes. We describe the generation of three ribozymes (Rz6, Rz21, Rz29) targeted to specific sites within the ErbB-4 mRNA open reading frame. We demonstrate that all three ErbB-4 ribozymes cleave ErbB-4 mRNA precisely and efficiently under physiological conditions in this cell free system. We also illustrate the intracellular efficacy and specificity of the ErbB-4 ribozymes in a model system (32D cell system). 32D cells are a murine hematopoietic IL3-dependent cell line that does not express detectable levels of endogenous EGF-family receptors. Overexpression of ErbB-4 receptors in 32D cells (32D/ErbB-4) abrogated IL-3-dependence by stimulation with NRG. We show that two of the ErbB-4 ribozymes (Rz6 and Rz29) were able to down-regulate ErbB-4 expression and were capable of abolishing the neuregulin-induced mitogenic effect in 32D/ErbB-4 cells. These results demonstrate that ribozyme Rz29 and Rz6 are biologically functional ribozymes.

Therefore, this invention relates to ribozymes, or enzymatic RNA molecules, directed to cleave mRNA species encoding specific sites in ErbB-4. In particular, applicants describe the selection and function of ribozymes capable of cleaving this RNA and their use to reduce activity of ErbB-4 in various tissues to treat the diseases discussed herein, more particularly, breast cancer. Such ribozymes are also useful for diagnostic applications.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript and efficient cleavage has been achieved in vitro [Jefferies, et al. (1989) *Nucleic Acid Res.* 17:1371].

Ribozymes act by first binding to a target RNA. Such binding occurs through the target RNA binding portion of a ribozyme which is held in close proximity to an enzymatic protion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action [Woolf, T. M. et al. (1992) *Proc. Natl. Acad. Sci. USA* 89:7305–7309]. Thus, the specificity of action of a ribozyme is greater than that of an antisense oligonucleotide binding the same RNA site. Consequently, the ribozyme agent will only affect cells expressing that particular gene, and will not be toxic to normal tissues.

The invention can be used to treat cancer or pre-neoplastic conditions. Two preferred administration protocols can be used, either in vivo administration to reduce the tumor burden, or ex vivo administration to eradicate transformed cells from tissues such as bone marrow prior to implantation.

Thus, in the first aspect the invention features an enzymatic RNA molecule (or ribozyme) which cleaves mRNA associated with development or maintenance of cancer, e.g. those mRNAs produced from the gene ErbB4 including mRNA targets disclosed in Table 1.

TABLE 1

| Nucleotide | mRNA target sequence | ID NOs |
|---|---|---|
| (60) | GAUUUGGGUCUGGUGAG | SEQ ID NO:1 |
| (210) | UGAGGUUGUCAUGGGC | SEQ ID NO:2 |
| (290) | GUCACAGGCUACGUGUUAG | SEQ ID NO:3 |

Hammerhead ribozymes (Rz) targeted to sites within ErbB-4 mRNA described in Table 1 were generated. These ErbB-4 ribozymes (Rz6, Rz21, Rz29) effectively catalyzed the precise cleavage of ErbB-4 mRNA under physiological conditions in a cell-free system. One of these ribozymes, Rz29, down-regulated ErbB-4 receptor expression by as much as 65%, with a corresponding 10-fold decrease in ErbB-4 tyrosine phosphorylation in a 32D cell model system. Furthermore, expression of this functional ErbB-4 ribozyme in T47D and MCF-7 human breast carcinoma cells led to a down-regulation of endogenous of ErbB-4 expression and a reduction of anchorage-independent colony formation.

By "enzymatic RNA molecule" it is meant an RNA molecule which has complementarity in a substrate binding region to a specified mRNA target, and also has an anzymatic activity which is active to specifically cleave that mRNA. That is, the enzymatic RNA molecule is able to intermolecularly cleave mRNA and thereby inactivate a target mRNA molecule. This complementarity functions to allow sufficient hybridization of the enzymatic RNA molecule to the target RNA to allow the cleavage to occur. One hundered percent complementarity is preferred, but complementarity as low as 50–75% may also be useful in this invention.

Ribozymes that cleave the specified sites in ErbB4 RNAs represent a novel therapeutic approach for the treatment of tumors and other conditions where overexpression of ErbB-4 is causal such as childhood medulloblastoma [Gilbertson, R. J. et al. (1998) Cancer Res. 58:3932–3941]. Applicants show that ribozymes are able to inhibit the activity of ErbB4 and that the catalytic acitiviy of the ribozymes is required for their inhibitory effect. Those of ordinary skill in the art, will find that it is clear from the examples described that other ribozyems that cleave these sites in ErbB4 RNAs may be readily designed and are within the scope of this invention.

In a second aspect, the invention features a mammalian cell which includes an enzymatic RNA molecule as described above. Preferably, the mammalian cell is a human cell.

In a third aspect, the invention features an expression vector which includes nucleic acid encoding an enzymatic RNA molecule described above, located in the vector, e.g., in a manner which allows expression of that enzymatic RNA molecule within a mammalian cell.

In a fourth aspect, the invention features a method for treatment of breast cancer by administering to a patient an enzymatic RNA molecule as described above.

The enzymatic RNA molecules of this invention can be used to treat human breast cancer. Such treatment can also be extended to other related genes in nonhuman primates. Affected animals can be treated at the time of cancer detection or in a prophylactic manner. This timing of treatment will reduce the number of affected cells.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

Figure 1:
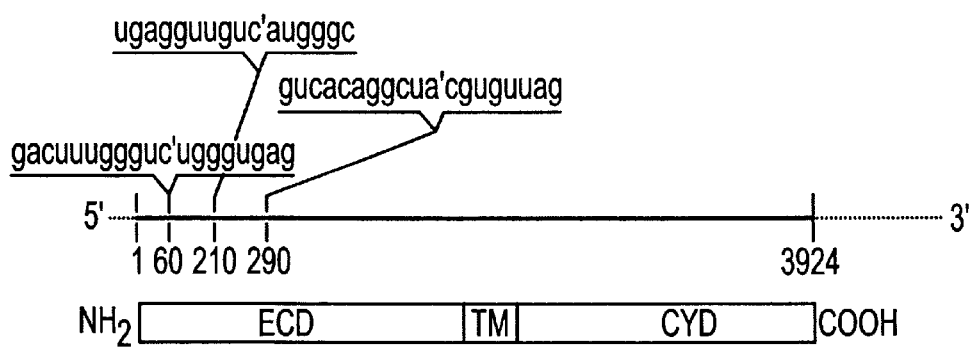
FIG. 1. Illustrates the ErbB-4 ribozymes targeted sequences and cleavage sites (seq ID No. 1,2,3) downstream of the translation initiation site in the ErbB-4 mRNA open reading frame. ECD, extracellular domain, TM, transmembrane domain, CYD, cytoplasmic domain.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding ErbB4 proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

In one of the preferred embodiments of the invention, the enzymatic nucleic acid molecule is formed in a hammerhead or hairpin motif, but may also be formed in a motif of a hepatitis d virus, group I intron, group II intron or RNaseP RNA (in association with an RNA guide sequence) or Neurospora VS RNA. Examples of such hammerhead motifs are described by Rossi et al. (1992) *AIDS Research and Human Retroviruses* 8:183; of haripin motifs by Hampel and Tritz, (1989) *Biochemistry* 28:4929, Feldstein et al. (1989) *Gene* 82:53; Haseloff and Gerlach (1989) *Gene* 82:43, and Hampel et al. (1990) *Nucleic Acids Res.* 18:299; of the hepatitis d virus motif is described by Perrotta and Been (1992) *Biochemistry* 31:16; of the RNaseP motif by Guerrier-Takada et al. (1983) *Cell* 35:849, Forster and Altman (1990) *Science* 249:783, Li and Altman (1996) *Nucleic Acids Res.* 24:835; *Neurospora* VS RNA ribozyem motif is described by Collins (Saville and Collins, (1990) *Cell* 61:685–696; Saville and Collins, (1991) *Proc. Natl. Acad. Sci. USA* 88:8826–8830; Collins and Olive, (1993) *EMBO J.* 14:363); Group II introns are described by Griffin et al. (1995) *Chem. Biol.* 2:761, Michels and Pyle (1995) *Biochemistry* 34:2965; and the Group I introns by Cech et al. U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Synthesis of nucleic acids greater than 100 nucleotides in length is difficult using automated methods, and the therapeutic cost of such molecules is prohibitive. In this invention, small nucleic acid motifs (e.g. antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters [Kashani-sabet et al. (1992) *Antisense Res. Dev.* 2:3–15; Dropulic et al. (1992) *J. Virol.* 66:1432–1441; Weerasinghe et al. (1991) *J. Virol.* 65:5531–5534; Ojwang et al. (1992) *Proc. Natl. Acad. Sci. USA* 89:10802–10806; Chen et al. (1992) *Nucleic Acids Res.* 20:4581–4589; Thompson et al. (1995) *Nucleic Acids Res.* 23:2259]. Those skilled in the art realize that any nucleic acid can be expressed in eukaryotic cells from the appropriate DNA/RNA vector. The activity of such nucleic acids can be augmented by their release from the primary transcript by a ribozyme [Ohkawa et al. (1992) *Nucleic Acids Symp. Ser.* 27:15–16; Taira et al. (1991) *Nucleic Acids Res.* 19:3249–3255; Chowrira et al. (1994) *J. Biol. Chem.* 269:25856].

Such ribozymes are useful for the prevention of the diseases and conditions discussed above, and any other diseases or conditions that are associated with the levels of ErbB4 activity in a cell or tissue. By "associated" is meant that the inhibition of ErbB4 RNAs and thus reduction in the level of respective protein activity will relieve to some extent the symptoms of the disease or condition. It may also mean that the occurence of such symptoms is correlated with the level of such RNAs.

Target Sites

Ribozymes targeting selected regions of mRNA associated with tumor cell growth are chosen to cleave the target RNA in a manner which preferably inhibits translation of the RNA. Genes are selected such that ihibition of translation will preferably inhibit cell replication, e.g. by inhibiting producition of a necessary protein. Selection of effective target sites within these critical regions of mRNA entails testing the accessibility of the target RNA to hybridization with various oligonucleotide probes. These studies can be performed using RNA probes and assaying accessibility by cleaving the hybrid molecule with RNAseH. Alternatively, such a study can use ribozyme probes designed from secondary cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The mRNA sequences are compared in an appropriate target region. Putative ribozyme cleavage sites are found. These sites represent the preferable sites for hammerhead ribozyme cleavage within these two target mRNAs.

The sequence of human and mouse ErbB-4 mRNA can be screened for accessible sites using a computer folding algorithm. Hammerhead or hairpin ribozyme cleavage sites are identified and are shown in Table 1. Other sites include all the GUX potential sites in the ErbB-4 mRNA. While mouse and human sequences can be screened and ribozyems thereafter designed, the human targeted sequences are of most utility. However, mouse targeted ribozymes are useful to test efficacy of action of the ribozyme prior to testing in humans.

Hammerhead ribozymes are designed that could bind and are individually analyzed by computer folding (Jaeger et al. (1989) *Proc. Natl. Acad. Sci. USA* 86:7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

DNA oligonucleotides representing potential hammerhead or hairpin ribozyme cleavage sites are synthesized. A polymerase chain reaction is used to generate a substrate for T7 RNA polymerase transcription from human or murine ErbB-4 cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a Phosphor Imaging system. From these data, hammerhead or hairpin sites are chosen as the most accessible.

Ribozymes of the hammerhead or hairpin motif are desined to anneal to various sites in the mRNA message. The binding arms are complementary to the target site sequences described above.

The ribozymes can be produced by gene transcription as described by Cech, supra, or by chemical synthesis as described by Usman et al. (1987) *J. Am. Chem. Soc.* 109:7845–7854 and in Scaringe t al. (1990) *Nucleic acids Res.* 18:5433–5441 and U.S. Pat. No. 5,599,704 to Thompson et al. and makes use of common nucleic acid protecting and coupling groups such as dimethoxytrityl at the 5'-end, and phosphoramidites at the 3'-end. The average stepwise coupling yields were >98%. Hairpin ribozymes are synthesized in two parts and annealed to reconstruct the active ribozyme [Chowrira and Burke (1992) *Nucleic Acids Res.* 20:2835–2840]. Hairpin ribozymes are also synthesized from DNA templates using bacteriophage T7 RNA polymerase [Milligan and Uhlenbeck (1989) *Methods Enzymol.* 180:51]. All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC) or other liquid chromatography techniques, employing reverse phase columns and anion exchangers on silica and polymeric supports. The purified ribozymes are resuspended in water.

The sequences of chemically synthesized ribozymes useful in this study are shown in Table I. Those in the art will recognize that these sequences are representative only of many more such sequences where the enzymatic portion of the ribozyme (all but the binding arms) is altered to affect activity. For example, stem-loop II sequence of hammerhead ribozymes can be altered (substitution, deletion, and/or insertion) to contain any sequences provided a minimum of two base-paired stem structure can form. Similarly, stemloop VI and VII can be altered (substitution, deletion, and/or insertion) to contain any sequence, provided a minimum of two base paired stem structure can form. The sequences listed in Table I can be formed of ribonucleotides or other nucleotides or non-nucleotides. Such ribozymes are equivalent to the ribozymes described specifically in the Table.

Ribozyme activity can be optimized, including altering the length of the ribozyme binding arms (stems I and III), or chemically synthesizing ribozymes with modifications that prevent their degradation by serum ribonucleases [Perrault et al. (1990) *Nature* 344:565; Pieken et al. (1991) *Science* 253:314; Usman and Cedergren (1992) *Trends in Biochem. Sci.* 17:334]. Various other chemical modifications can be made to the sugar moeities of enzymatic RNA molecules. Modifications which enhance their efficacy in cells, and removal of stem II bases to shorten RNA synthesis times and reduce chemical requirements are described in U.S. Pat. No. 5,334,711. All documents cited herein supra and infra are hereby incorporated in their entirety by reference thereto.

Selected ribozymes can be administered prophylactically, or to patients having breast cancer, e.g. by exogenous delivery of the ribozyme to an infected tissue by means of an appropriate delivery vehicle, e.g. a liposome, a controlled release vehicle, by use of iontophoresis, electroporation or ion paired molecules, or covalently attached adducts, or by incorporation into other vehicles, such as hydrogels, cyclodextrins, biodegradable nanocapsules, bioadhesive microspheres, and other pharmacologically approved methods of delivery. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of administration include intramuscular, intravascular, subcutaneous or joint injection, aerosol inhalation, oral (tablet or pill form), topical, systemic, ocular, intraperitoneal and/or intrathecal. Expression vectors for immunization with ribozymes and/or delivery of ribozymes are also suitable. The dosage will depend upon the disease indication and the route of administration but should be between 100–200 mg/kg of body weight/day. The duration of treatment will extend through the course of the disease symptoms, possibly continuously. The number of doses will depend upon disease delivery vehicle and efficacy data from clinical trials. A more detailed description of delivery methods is found in U.S. Pat. No. 5,599,704 by Thompson et al.

Another means of accumulating high concentrations of a ribozyme within cells is to incorporate the ribozymeencoding sequences into a DNA expression vector. Transcription of the ribozyme sequences is driven from a promoter for eukaryotic RNA polymerase I (pol I), RNA polymerase II (pol II), or RNA polymerase III (poly III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells [Gao and Huang (1993) *Nucleic Acids Res.* 21:2867–2872; Lieber et al. (1993) *Methods Enzymol.* 217:47–66]. Several investigators have demonstrated that ribozymes expressed from such promoters can function in mammalian cells [Lisziewicz et al. (1993) *Proc. Natl. Acad. Sci. USA* 90:8000–8004]. The above ribozyme transcription units can be incorporated into a variety of vectors for introduction into mammalian cells, including but not restricted to, plasmid DNA vectors, viral DNA vectors, (such as adenovirus or adeno-associated virus vectors), or viral RNA vectors (such as retroviral or alphavirus vectors). Viral vectors have been used to transfer genes and lead to either transient or long term gene expression [Zabner et al. (1993) *Cell* 75:207; Carter (1992) *Curr. Opi. Biotech.* 3:533].

The ribozymes of the present invention are also useful as diagnostic tools to specifically or non-specifically detect the presence of a target RNA in a sample. That is, the target RNA, if present in the sample, will be specifically cleaved by the ribozyme, and thus can be readily and specifically detected as smaller RNA species. The presence of such smaller RNA species is indicative of the presence of the target RNA in the sample.

The following MATERIALS AND METHODS were used in the examples that follow.

Materials and Methods

Cell lines and cell culture: The 32D murine hematopoietic cell line (40) and its derivatives were grown in RPMI (Cellgro) supplemented with 12% fetal calf serum (Biofluids) and interleukin-3 (IL-3) supplied as 6% conditioned medium from the WEHI-3B murine mylomonocytic leukemia cell line.

Plasmid construction: Two synthetic single-stranded ribozyme oligonucleotides were subcloned into the mammalian vector pCR3. The sequence and orientation of the inserts were confirmed by dideoxynucleotide sequencing of the construct using the Sequenase kit, version 2.0 (U.S. Biochemical Corp., Cleveland, Ohio). ErbB-4 ribozyme sequences:

Rz 6: 5'AAU UCG GCU CAC CCA CUG AUG AGU CCG UGA GGA CGA AAC CCA AAG UCCC3'; SEQ ID NO:4

Rz 21: 5'AAU UCG UUG CCC AUC UGA UGA GUC CGU GAG GAC GAA ACA ACC UCA CC3'; SEQ ID NO:5

Rz 29: 5'AAU UCC ACU AAC ACG CUG AUG AGU CCG UGA GGA CGA AAG CCU GUG ACUC3'; SEQ ID NO:6

Ribozyme mediated mRNA cleavage in vitro: The substrate ErbB-4 cDNA fragment was derived by RT-PCR with RNA from MDA-MB-453 cells, which express relatively high levels of ErbB-4. The PCR primers for subcloning of ErbB-4 cDNA: 5' primer sequence: $^{5'}$AAT TGT CAG CAC GGG ATC TGA GAC$^{3'}$ (SEQ ID NO:7), and 3' primer sequence $^{5'}$GTT TCC TTA AAC AAG ACC AGA TGT$^{3'}$ (SEQ ID NO:8). The RT-PCR products were then cloned into the PCR3 vector. Clones were sequenced to verify that they contained the ErbB-4 cDNA fragment. We then performed in vitro run-off transcripts from an ErbB-4 cDNA construct to generate the ErbB-4 ribozyme substrate. Likewise, ribozymes were chemically synthesized as DNA oligonucleotide and subsequently synthesized in vitro by utilizing the T7 RNA polymerase. Cleavage reactions were performed in 50 mmol/L Tris-HCl, pH8.0, and 20 mmol/L MgCl$_2$. Substrate and ribozyme transcripts were then mixed and incubated at 50° C. for 30 min. Reaction products were analyzed on 6% urea polyacrylamide gel, and products were detected by autoradiography.

Transfection by electroporation: 1×10$^7$ 32D derivative cells were used for each transfection. 10 ug of plasmid DNA was added to cells resuspended in 300 ul of PBS. Cells were electroporated at 250 volts, using a BioRad electroporation system, plated onto 100 mM dishes, and incubated for 24 hr. The cells were then selected in growth medium containing 750 ug/ml geneticin (G418-sulfate, Gibco).

Northern blot analysis: Messenger RNA (mRNA) isolation using RNasol B(Tel-Test, Inc. Texas ). 20 ug of total RNA from each cell line was used to hybridize with an ErbB-4 cDNA probe and autoradiographed for 48 hr.

Autophosphorylation of erbB-family receptors: A total of 2×10$^8$ 32D derivative cells were washed in phosphate-buffered saline (PBS) and resuspended in 50 ml of RPMI supplemented with IL-3, and incubated for 4 hr. at 37° C. Following incubation, cells were washed in PBS, and resuspended in 1 ml of PBS with Na$_3$(VO)$_4$. Remaining steps were performed on ice. Recombinant heregulin β3 isoform (EGF-like domain) was added at a final concentration of 150 ng/ml. Following a 10 min incubation, cells were lysed in "Hepes-Lysis buffer" and the cell debris was pelleted by centrifugation.

The lysates were then immunoprecipitated with either anti-EGFR (Ab-1, Oncogene Science, Uniondale, N.Y.), anti-erbB-2 (Ab-3, Oncogene Science, Uniondale, N.Y.), anti-erbB-3 (C17, Santa Cruz Biotechnology, Santa Cruz, Calif.) or anti-erbB-4 (C18, Santa Cruz Biotechnology, Santa Cruz, Calif.) in combination with protein-A agarose (Pharmacia, Piscataway, N.J.) overnight at 4° C. with gentle agitation. Detail see elsewhere [Tang, C. K. et al. (1996) *Cancer Research* 56:3350–3358].

Fluorescence-activated cell sorter (FACStar) analysis: 1×10$^6$ cells were harvested and then stained for one hour with an anti-ErbB-4 monoclonal antibody (Ab-1, NeoMarker), then a secondary FITC-anti-mouse antibody was used and the ErbB-4 level in each cell was quantitatively measured by flow-cytometry.

Anchorage-independent growth assay: A bottom layer of 0.1 ml IMEM containing 0.6% agar and 10% FCS was prepared in 35 mm tissue culture dishes. After the bottom layer solidified, cells (10,000 per dish) were added in a 0.8 ml top layer 0.4% Bacto Agar, and 5% FCS. All samples were prepared in triplicate. Cells were incubated for approximately 12 days at 37° C. Colonies larger than 60 um were counted in a cell colony counter (Ommias 3600, Imaging Products Int., Inc. Charley, Va.)

Mitogenic assay: 32D transfected cells were plated at a density of 1×10$^4$ cells with or without IL3 supplement, or supplemented with 100 ng/ml of HRG in the absence of IL-3. Two days post plating, the cells were labeled with $^3$[H]thymidine for two hours. $^3$[H]thymidine incorporation was then analyzed by β-scintillation counter.

In vitro Kinase Assay: 32D/E4, 32D/E4+V and 32D/E4+Rz29 cells were serum starved for 2 hours prior to treatment with or without 100 ug/ml of HRG. Cells then lysed in lysis buffer. 400 ug of total protein of each cell line was used to immunoprecipitate with anti-ErbB-4 anti-body (C18, Santa Cruz Biotechnology, Santa Cruz, Calif.) in combination with protein-A agarose (Pharmacia, Piscataway, N.J.). Reactions were carried as described previously [Goldstein, D. J. et al. (1992) *EMBO J.* 11:4951–4959]. Briefly, to the washed beads 50 ul of a solution containing 10 mM Tris-HCL, pH 7.5, 10 mM MgCl$_2$, 10 mM MnCl$_2$, 10 $\mu$Ci[γ-$^{32}$P]ATP and 1ug aprotinin was added for 25 min at room temperature. Reactions were terminated by spinning down the Sepharose beads in a microcentrifuge, discarding the supernatant and resuspending the beads in 50 ul SDS gel loading buffer. Eluted proteins were analyzed by SDS-PAGE and autoradiography.

In vivo studies. Athymic nude mice were inoculated subcutaneously with either wild type cells or ErbB-4 ribozyme transfected cells. We injected 5×10$^6$ cells/site, two sites per mice in the presence of estrogen pellets. Because T47D cells are estrogen dependent cell line, estrogen is required for tumor growth. Estrogen pellets (60 days release) were implanted subcutaneously into the cervical scapular space. The size of the tumors were measured biweekly.

EXAMPLE 1

Figures 2A, 2B:
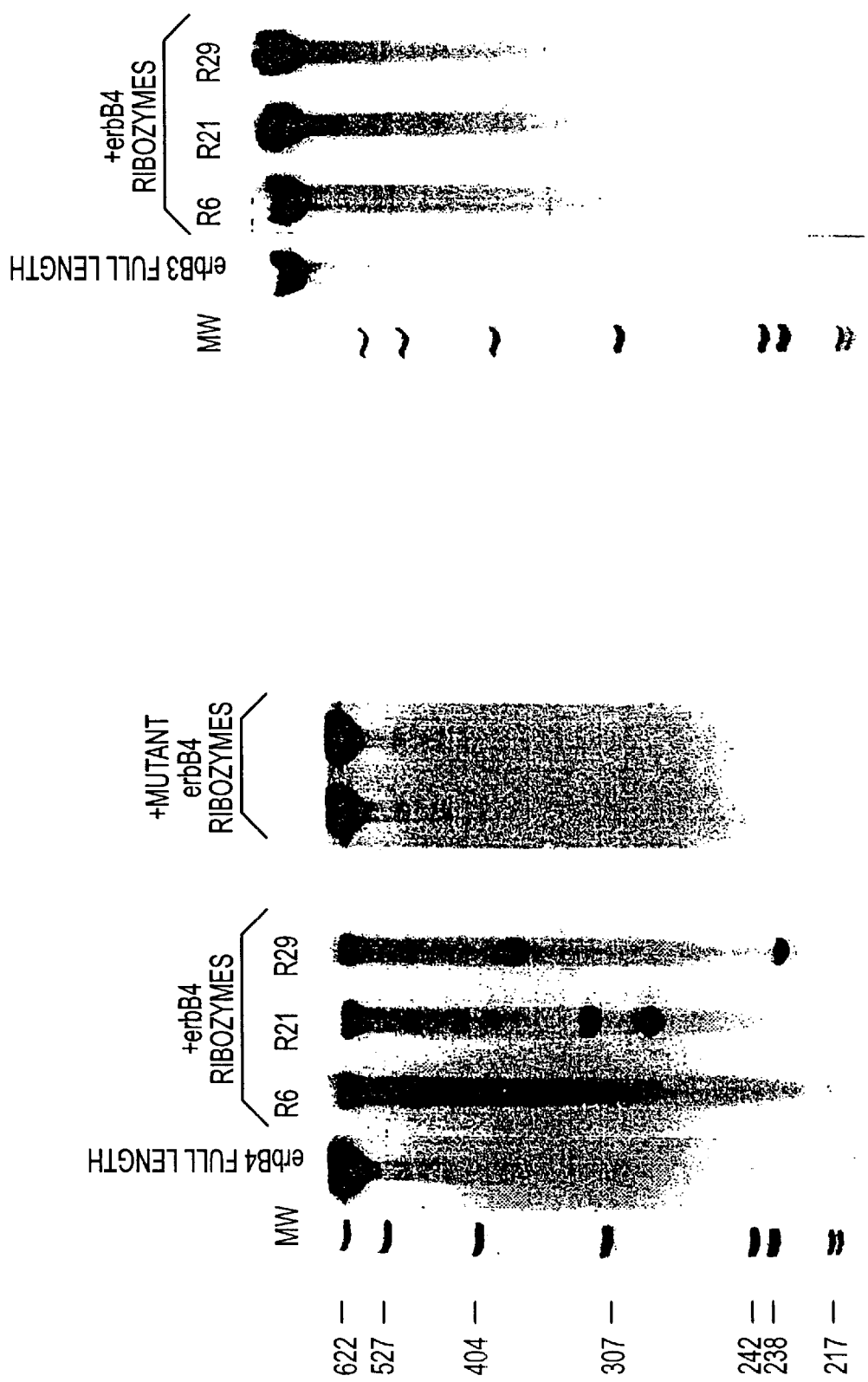
FIGS. 2, A and B. Catalytic activity of ErbB-4 ribozyme in an extracellular system. Lane 1 represents molecular weight markers. Lane 2, $^{32}$P-labeled ErbB-4 transcript with an expected size of 622 nucleotides (nts). Lanes 3–5, cleavage products of the three ErbB-4 ribozymes (Rz6: 518, 110nts; Rz21: 285, 337nts; Rz29: 232, 390nts). Lanes 6, 7, mutant ribozymes do not cleave ErbB-4 transript. B) Lane 1, molecular weight marker. Lane 2, $^{32}$P-labeled ErbB-3 transcript with an expected size of 698 nucleotides.

Generation and Demonstration of ErbB-4 Ribozyme Efficacy and Specificity in a Cell Free System To investigate the biological significance of ErbB-4 in human breast cancer cells, we used molecular targeting of the ErbB-4 mRNA by ribozymes. Three ribozymes (Rz6, Rz21, Rz29) targeted to specific sites within the ErbB-4 mRNA open reading frame were generated. These ribozymes were modeled on the previously described hammerhead structure [Zuker, M. and Stiegler, P. (1981) *Nucleic Acids Res.* 9:133–148; McCall, M. J. et al. (1992) *Proc. Natl. Acad. Sci. USA* 89:5710–5714], derived and minimized to the catalytic center portion of 22 nucleotides. The targeted cleavage sites selected for the design of the ribozymes were 60(Rz6), 210(Rz21) and 290(Rz29) nucleotides downstream of the translation initiation site of the ErbB-4 mRNA (FIG. 1). The catalytic activity of these ribozymes was first evaluated in an extracellular system. All three ErbB-4 ribozymes cleaved ErbB-4 mRNA precisely and efficiently under physiological conditions in this cell free system (FIG. 2A, Lanes 2–5). Cleavage was specific as the actual sizes of the cleaved fragments correspond to the expected sizes if cleavage were to occur immediately 3' to the GUN sequence. As a control for specificity, catalytically inactive mutant ribozymes were engineered. Point mutation of G to A in the catalytic domain of either Rz29 or Rz6 (FIG. 2A, lanes 6 and 7) resulted in loss of catalytic activity as predicted by previously reported mutational studies of McCall et al. (1992, supra). The specificity of these three ErbB-4 ribozymes was evaluated on a non-specific mRNA substrate. As expected, no cleavage was observed following incubation of these ribozymes with ErbB-3 mRNA (FIG. 2B). These results indicate that all three of the GUN sequences chosen in the ErbB-4 mRNA are accessible to ribozyme-mediated cleavage in an extracellular system.

EXAMPLE 2

An Intracellular Model System for Evaluating the Specificity and Efficacy of ErbB-4 Ribozymes We next investigated the catalytic activity of these ribozymes in a model cellular system. Although the ribozyme sensitivity in an extracellular system can be correlated with the predicted secondary structure of the target RNA, the intracellular susceptibility of the target RNAs to ribozymes does not necessarily correlate with their predicted secondary structure. In addition, the complexity of heterodimerization and transphosphorylation between the ErbB family members in breast cancer cells makes it difficult to determine the specificity of ErbB-4 ribozymes. Furthermore, the goal of these ribozymes is to interrupt gene expression. If ErbB-4 is critical for cell proliferation, its down-regulation may be lethal. Thus, an ideal system for screening the intracellular enzymatic activity of these ribozymes requires the following criteria: 1) Expression of high levels of ErbB-4 receptor; 2) No expression of other EGF family receptors; 3) Non-lethality of ErbB-4 ribozyme introduction; and 4) Easy detection of ribozyme activity by bioassay. We therefore used the 32D cell system to examine the intracellular efficacy and specificity of the ErbB-4 ribozymes. 32D cells are a murine hematopoietic IL3-dependent cell line that does not express detectable levels of endogenous EGF-family receptors. Studies have shown that IL-3-dependence can be abrogated by introduction of foreign growth factor receptor genes followed by stimulation with the appropriate growth factor [Pierce, J. H. (1990) Adv. Regul. Cell Growth 2:275–297]. The ability of ErbB-4-expressing cells to bypass the IL-3-dependent pathway following HRG activation [Alimandi, M. et al. (1997) *EMBO J.* 16: 5608–5617], provides a simple growth assay to determine the biological function of these ribozymes intracellularly.

EXAMPLE 3

Figure 3:
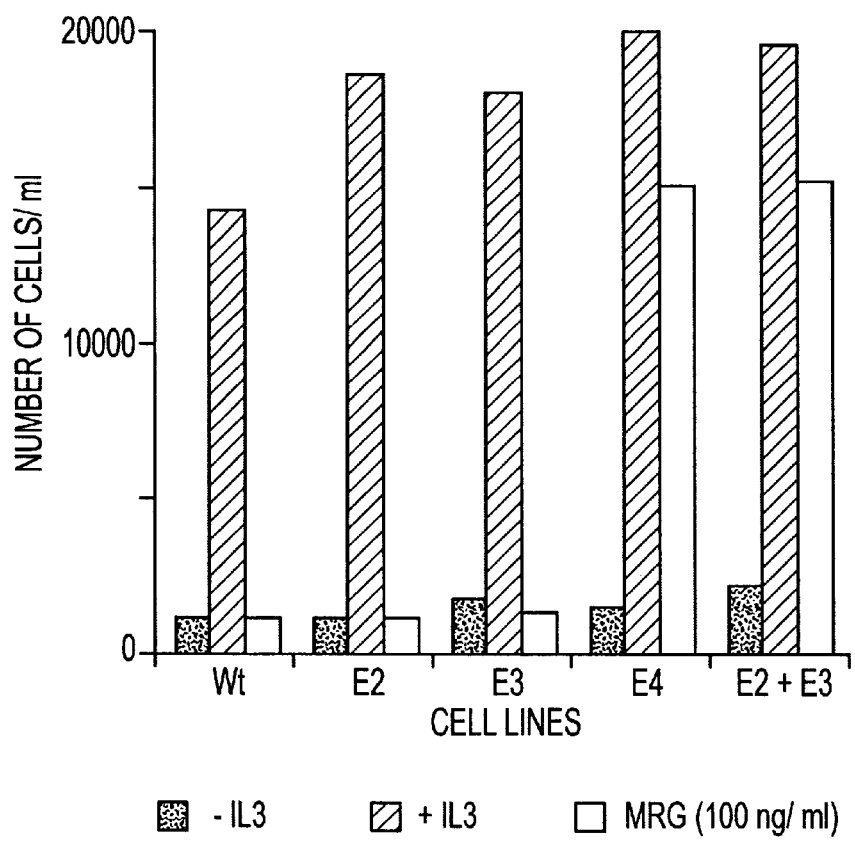
FIG. 3. Growth assay: 32D cells were plated at a density of $1\times10^4$ cells/ml in IL3 free medium, medium supplemented with IL-3, or in medium lacking IL-3 but supplemented with 100 ng/ml of human recombinant HRG. Viable cells were counted on day 3 after seeding. Hereregulin can induce Il-3-independent growth in 32D/E4 and 32D/E2+E3 cells. All samples were prepared in triplicate. This assay was repeated more than three times. The SD was within 10%.
Figure 4:
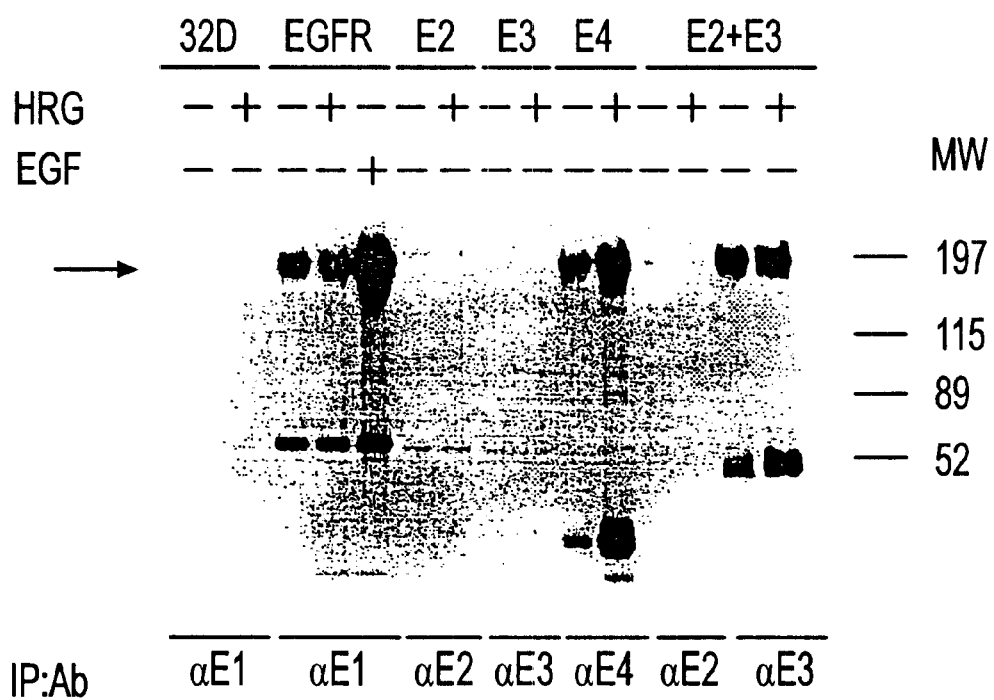
FIG. 4. Regulation of receptor tyrosine phosphorylation by HRG in 32D/E4 and 32D/E2+E3 cells. 500 ug of lysates from untreated or HRG (100 ng/ml for 5 minutes) treated 32D transfectants (32D/wt, 32D/E2, 32D/E3, 32D/E4, 32D/E2+E3) were immunoprecipitated with anti-receptor antibodies (αE2, αE3, αE4). 32D/EGFR cells (E1) were treated with 100 ng/ml of EGF for 5 minutes and immunoprecipitated with anti-EGFR antibody (αE1). Lysates from EGF or HRG-treated cells are denoted '+' while lysates from untreated cells are denoted '−'. The precipitates were then subjected to Western blotting with an anti-phosphotyrosine antibody (UBI, Lake Placid, N.Y.). MW, Molecular Weight; IP, immunoprecipitation.

Biological Function of EGF Family Receptors in 32D Cells 32D cell transfectants that express the EGF receptor family members individually and in pairwise combinations (Alimandi et al., 1997, supra). The resultant stably transfected cells were designated as 32D/E1, 32D/E2, 32D/E3, 32D/E2+E3 and 32D/E4, where E1, E2, E3 and E4 refer to EGFR, ErbB-2, ErbB-3 and ErbB-4 receptors, respectively. The high levels of receptor expression was confirmed by Western blotting or immunoprecipitation followed by Western blotting (data not shown). No detectable levels of endogenous EGF family receptor expression were found in parental 32D cells. In the absence of cognate ligands, all of the 32D transfected cells remained dependent on IL-3 for survival [Di Fiore, P. O. et al. (1990) *Science* 248:79–83]. 32D transfectants were tested for induction of IL-3-independent survival or proliferation. Consistent with previous studies (Alimandi et al., 1997, supra and Di Fiore et al., 1990, supra), untransfected parental cells did not proliferate or survive following HRG stimulation. Cells transfected with ErbB-4 or co-expressing ErbB-2 and ErbB-3, bypassed the IL3-dependent pathway in response to HRG stimulation, but cells transfected with ErbB-2 or ErbB-3 alone did not survive and proliferated in an IL-3-dependent manner (FIG. 3). Regulation of tyrosine phosphorylation of each receptor by HRG was evaluated by immunoprecipitating the corresponding receptors and immunoblotting with antiphosphotyrosine. FIG. 4 demonstrates that no autophosphorylation was observed in the parental cells (32D) in the presence of HRG. In both EGFR- and ErbB-4-expressing cells, the receptors were constitutively phosphorylated; however, phosphorylation could be further induced following exposure to its cognate ligands. 32D/E2 cells demonstrated significant phosphorylation of ErbB-2 in the absence of HRG, but receptor phosphorylation was not elevated in the presence of HRG (FIG. 4). No phosphorylation was observed in the presence or absence of HRG in 32D/E3 cells. In 32D/E2+E3 cells, a high basal level of phosphorylated ErbB-3 was observed, and increased phosphorylation was observed following HRG stimulation (FIG. 4). Thus, the 32D cells provide an ideal system to study the specificity and efficacy of the ribozymes targeting the ErbB-family receptors.

EXAMPLE 4

Demonstration of ErbB-4 Ribozyme Catalytic Activity in 32D Cells

ErbB-4 ribozymes abolish HRG-induced IL3-independence

All three ErbB-4 ribozymes were cloned into a mammalian expression vector downstream of the CMV early promoter. We then transfected the ErbB-4 Rz into 32D/E4 cells. We hypothesized that the functional ribozymes would down-regulate ErbB-4 expression and thereby reduce or abolish the HRG-induced, IL-3-independent survival or proliferation. ErbB-4 Rz transfected cells were tested for growth in the presence and absence of HRG. Cell lines expressing one of the ErbB-4 ribozymes (Rz29), failed to respond to HRG and proliferated in an IL-3-dependent manner. In contrast, parental 32D/E4 and vector alone-transfected cells responded to HRG and proliferated in the absence of IL-3. Rz6 partially inhibited the HRG effect. In contrast, Rz21 had no effect on responsiveness to HRG stimulation. Table 2 summarizes the ribozyme effects in these ErbB-4 cells. We next evaluated the specificity of the ErbB-4 ribozymes by expressing all three ErbB-4 ribozymes in 32D/E2+E3 cells. No effect on the HRG-induced IL3-independent survival and proliferation was observed. We then evaluated the efficacy of the ribozyme by using an ErbB-2 ribozyme, which has been shown to down-regulate ErbB-2 mRNA specifically in a previous study (Personal communication), to target ErbB-4 mRNA. In contrast to the ErbB-4 ribozyme, this ErbB-2 ribozyme did not alter the HRG-induced IL3-independence of ErbB-4-expressing 32D cells. These data suggest that Rz6 and Rz29 are functional ribozymes, and that the effects of these ErbB-4 ribozymes are highly specific to the ErbB-4 receptor mRNA. Rz29 exhibits a higher level of biological activity compared to Rz6. Rz21 apparently is a non-functional ribozyme in 32D cells. The inability of Rz21 to mediate the down regulation of ErbB-4 may be due to several possibilities. For example, the target site may not accessable intracellularly, or Rz21 may be unstable in 32D cells.

TABLE 2

Effect ot ErbB-4 ribozymes on the density of 32D/E4 cells in response to IL-3 starvation and HRG stimulations

| Cell line | Number of viable cells (×1000 cells/ml) | | |
|---|---|---|---|
| | −IL-3 | +IL-3 | +HRG/−IL-3 |
| E4 | 1.3 | 1996 | 1490 |
| E4/Vector | 1 | 1894 | 1369 |
| E4/Rz6 | 1.1 | 1717 | 367 |
| E4/Rz21 | 1 | 1845 | 1300 |
| E4/Rz29 | 1.2 | 1823 | 56 |
| E4/ErbB-2 ribozyme | 1.2 | 1798 | 1279 |
| E2 + E3/Rz6 | 1.1 | 1869 | 1307 |
| E2 + E3/Rz21 | 1 | 1946 | 1377 |
| E2 + E3/Rz29 | 1.2 | 1854 | 1298 |

EXAMPLE 5

ErbB-4 Ribozyme Abolishes the HRG Stimulation of Mitogenesis

Figure 5:
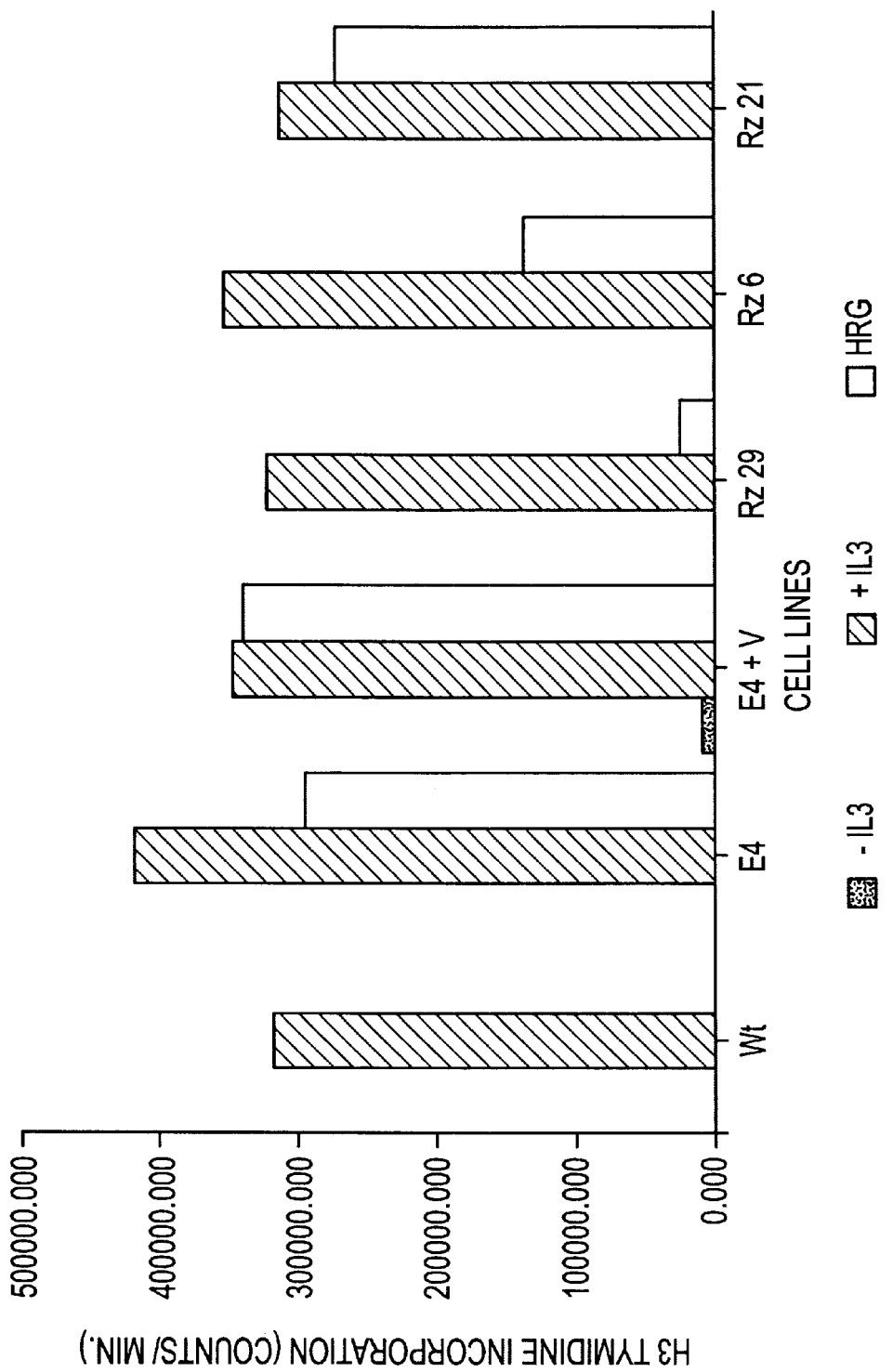
FIG. 5. ErbB-4 ribozyme abolishes HRG-induced mitogenesis. 32D-transfected cells were plated at a density of $1 \times 10^4$ cells with or without IL-3, or with 100 ng/ml HRG in the absence of IL-3. Two days after plating, the cells were labeled with $^3[H]$thymidine for two hours. $^3[H]$ thymidine incorporation was then analyzed by scintillation counting. The parental 32D cells are labeled as 'wt'. 32D/E4 transfected cells are denoted as E4. E4+V represents the empty vector transfected 32D/E4 cells. Ribozyme transfected cells are indicated as Rz6, Rz21 and Rz29. Rz29 abolished the HRG induced IL-3-independent growth. All samples were prepared in triplicate. This assay was repeated three times. The SD was within 10%.
Figure 6A:
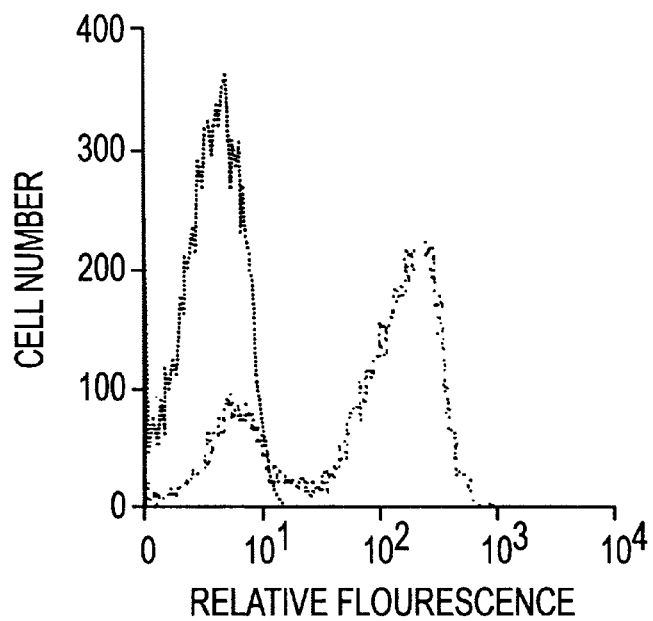
FIGS. 6A–D. Rz29 down-regulation of ErbB-4 expression in 32D/ErbB-4 cells. The levels of ErbB-4 in 32D/E4 and Rz29 transfected 32D/E4 cells were quantitatively measured by flow-cytometry. $1 \times 10^6$ cells were harvested and stained with an anti-ErbB-4 monoclonal antibody in combination with fluorescence-labeled anti-mouse IgG antibody and analyzed by FACScan. A) Expression of ErbB-4 in vector-transfected cells (E4/V). Right-hand curves, specific staining; left-hand curves, nonspecific staining (primary antibody omitted); ordinates, relative cell number; abscissas, log fluorescence. B) Rz29 down-regulates ErbB-4 expression by 50%. Dotted-line curve, ErbB-4 expression in ErbB-4/V cells. Solid-line curve, ErbB-4 expression in Rz29-transfected cells. C) Rz 21 has no effect on ErbB-4 expression. Dotted-line curve, ErbB-4 expression in ErbB-4/V cells. Solid-line curve, ErbB-4 expression in Rz21 transfected cells. D) Rz6 down-regulates ErbB-4 expression by 30%. Dotted-line curve, ErbB-4 expression in ErbB-4/V cells. Solid-line curve, ErbB-4 expression in Rz6 transfected cells.
Figure 6B:
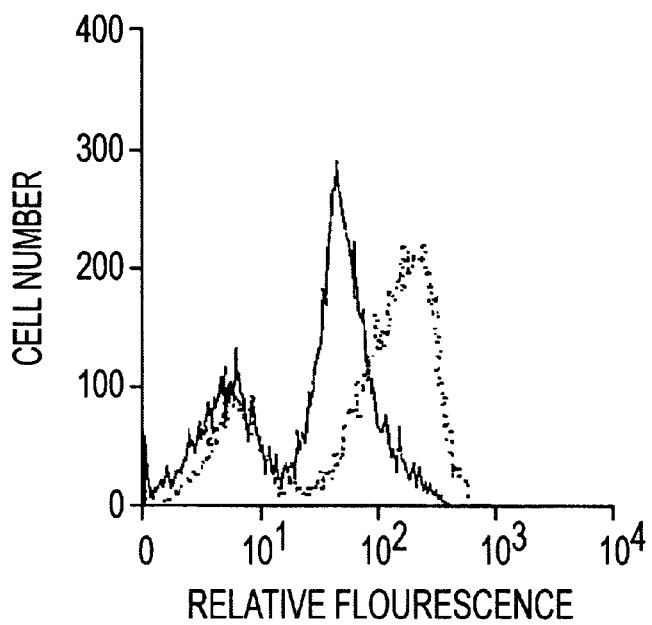
Figure 6C:
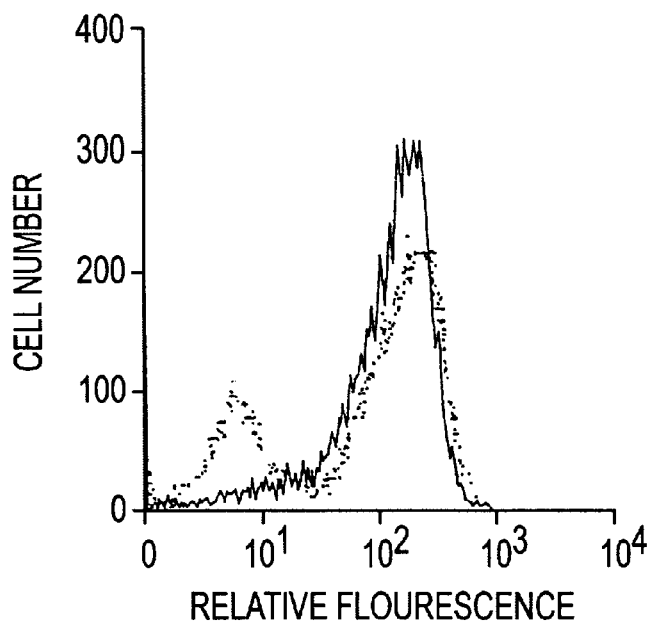
Figure 6D:
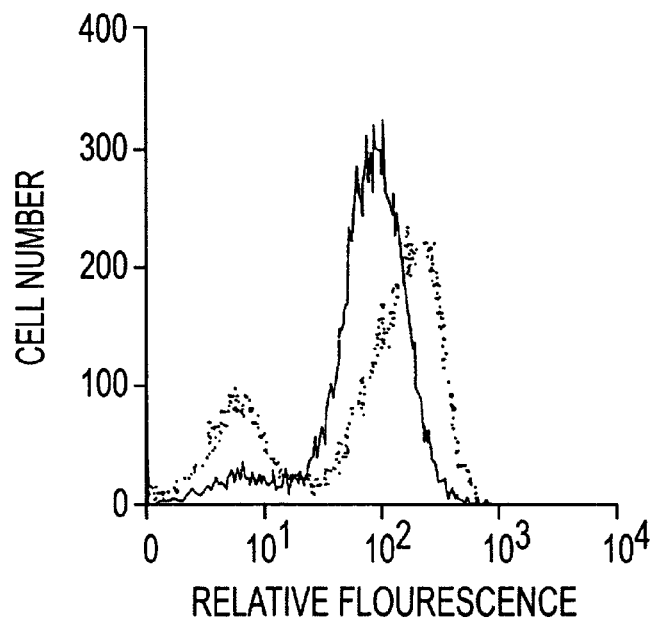

To confirm the growth inhibitory activity of the ErbB-4 ribozymes, a mitogenic assay to measure DNA synthesis was performed on ErbB-4 Rz-transfected cells. As shown in FIG. 5, all the 32D transfected cells exhibited very low levels of [$^3$H]thymidine incorporation in the absence of IL-3. In contrast, all the 32D transfected cells exhibited high levels of [$^3$H]thymidine incorporation in the presence of IL-3, as expected. In the 32D/E4 control cells, HRG stimulated high levels of [$^3$H]thymidine incorporation in the absence of IL-3; whereas the [$^3$H]thymidine incorporation was almost completely abolished in the Rz29- transfected cells. [$^3$H]thymidine incorporation was significantly reduced in Rz6-transfected cells, but to a lesser extent than in Rz29-transfected cells. No significant changes in the Rz21-transfected cells were observed. These results were thus consistent with the growth assay.

EXAMPLE 6

ErbB-4-Rz-mediated Down-regulation of ErbB-4 Expression in 32D/ErbB-4 Cells

To evaluate the intracellular enzymatic cleavage activity of ErbB-4 ribozymes, the ribozyme transfectants were examined for ErbB-4 mRNA levels by Northern blot analysis. Rz6- and Rz29-expressing cells exhibited significantly reduced ErbB-4 mRNA levels relative to control cells or to Rz21-expressing cells (data not shown). Thus, the abolishment of the HRG-induced IL-3 independent biological effect correlates with reduction of ErbB-4 mRNA levels in these cells.

To further characterize the ribozyme effect, we quantitatively examined the ErbB-4 ribozyme-mediated down-regulation of ErbB-4 receptor expression in these ErbB-4Rz transfected cells by FACS analysis. Consistent with Northern analysis, Rz29- and Rz6-transfected cells expressed significantly less cell surface ErbB-4 receptor relative to the 32D/E4 control cells (65% and 45% less ErbB-4, respectively; FIG. 6). No significant reduction of ErbB-4 expression was detected in R21-transfected cells. Taken together, these data suggest that the ErbB-4 Rz29 and Rz6 are biologically functional ribozymes.

EXAMPLE 7

Reduction of Autophosphorylation by ErbB-4 Ribozymes

Figure 7:
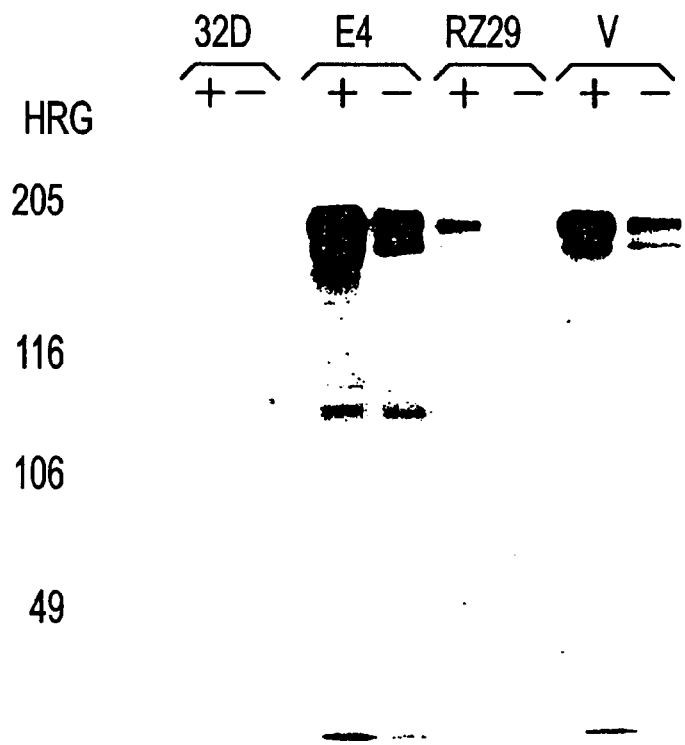
FIG. 7. Reduction of autophosphorylation of ErbB-4 receptor by Rz29 ribozyme. Cells were treated with (+) or without (−) HRG (100 ng/ml) for 5 minutes prior to lysis, and 400 ug of lysates were immunoprecipitated with specific anti-ErbB-4 antibody. Precipitated proteins were then used for in vitro kinase assay as described in Material and Methods below. Lysates from 32D wild-type and transfected cells are indicated above. 32D, untransfected cells; E4, ErbB-4 transfected cells; Rz29, ErbB-4 ribozyme Rz29-expressing 32D/E4 cells; V, cells transfected with empty vector. Molecular weight standards are shown on the left-hand side of the gel.
Figure 8:
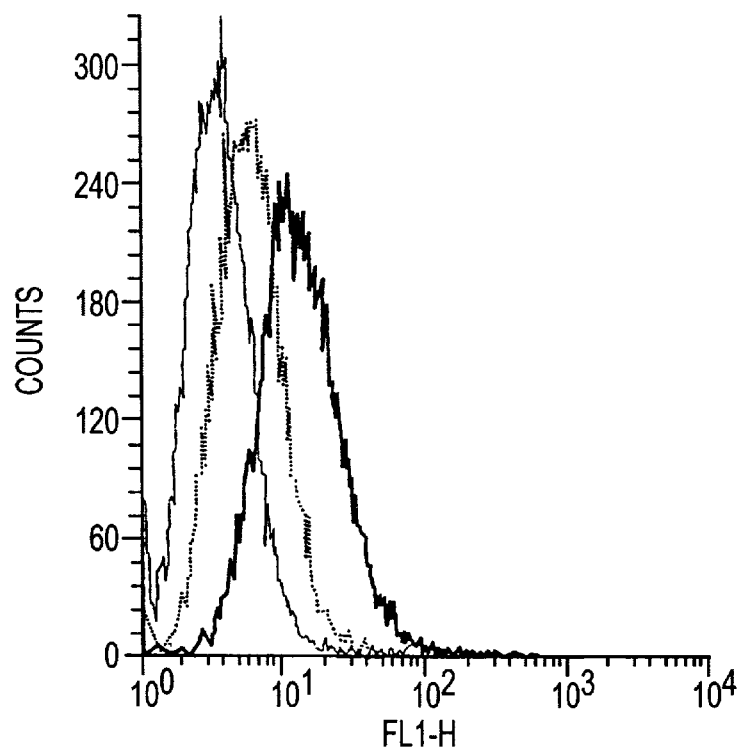
FIG. 8 ErbB-4 ribozyme down-regulation of endogenous ErbB-4 expression in T47D human breast cancer cells. The level of ErbB-4 in T47D/wt and T47D/Rz pool clones were quantitatively measured by flow-cytometry. $1 \times 10^6$ cells were harvested and stained with an anti-ErbB-4 monoclonal antibody in combination with fluorescence-labeled anti-mouse IgG antibody and analyzed by FACScan. Left-hand curve (thin line curve) represents nonspecific staining (primary antibody omitted). Right-hand curve (Bold line curve) represents the ErbB-4 expression in T47D wild-type cells. The dotted-line curve (middle curve) represents the ErbB-4 expression in Rz6 transfected cells. The ordinates, relative cell number; abscissas, log fluorescence.

To determine whether the HRG-induced IL-3-independent phenotype in ErbB-4 transfectants correlated with an increase in receptor tyrosine phosphorylation, the autophosphorylation of the receptors in these cells was examined by a kinase assay. FIG. 7 demonstrates that the level of ErbB-4 intrinsic tyrosine kinase activity in Rz29-transfected cells was markedly reduced compared to control transfectants (32D/E4 and 32D/E4/Vector). Because ErbB-4 expression was down-regulated only 65% by Rz29, the cells still express ErbB-4 receptors. HRG was therefore still able to induce the phosphorylation of the remaining ErbB-4 receptors. However, the level of phosphorylation was significantly lower than the 32D/E4 cells or the vector transfected cells (32D/E4/V). Reduction of phosphorylation correlated with reduction in expression of ErbB-4. Furthermore, these data also imply that while Rz29 is specifically cleaving its target mRNA, it does not affect the function of those receptors that are expressed. Taken together, these intracellular experiments demonstrated that the decrease of ErbB-4 protein production, activation and mRNA expression correlate with the ErbB-4 ribozyme catalytic activity.

EXAMPLE 8

The Effect of Down-regulation of ErbB-4 Receptor in Human Breast Cancer Cells

Figure 9:
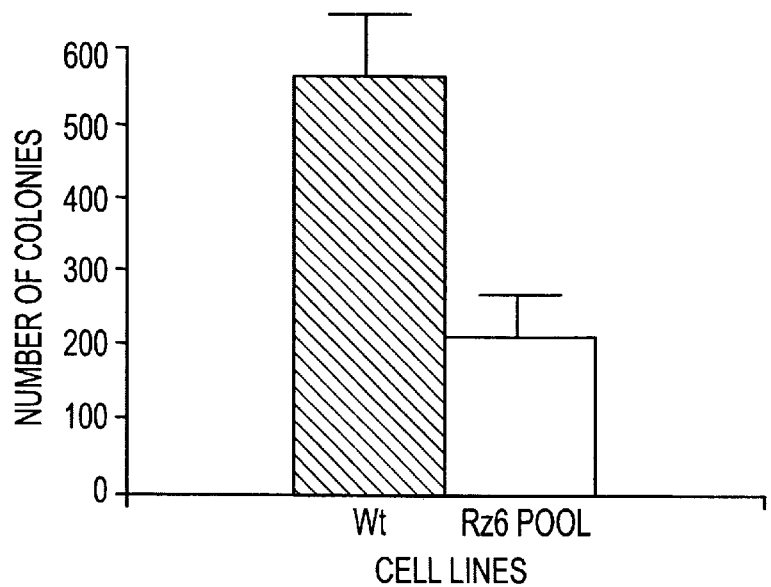
FIG. 9. Anchorage-independent growth assay: Expression of ErbB-4 ribozyme in T47D cells (T47D/Rz6 pool clone) inhibits colony formation by more than 50%. A bottom layer of 0.1 ml Iscove's modified Eagle's medium (IMEM) containing 0.6% agar and 10% FCS was prepared in 35 mm tissue culture dishes. After the bottom layer solidified, cells (10,000 per dish) were added on a 0.8 ml top layer containing 0.4% Bacto Agar, and 5% FCS. All samples were prepared in triplicate. The cells were incubated for approximately 12 days at 37° C. Colonies larger than 60 um were counted in a cell colony counter.

To investigate the biological and biochemical functions of ErbB-4 in human breast cancer, we expressed the ErbB-4 ribozymes in several ErbB-4-positive human breast cancer cell lines. Four human breast cancer cell lines were selected as recipient cells: T47D, MCF-7, MDA-MB-453 and MDA-MB-231. In T47D and MCF-7 cells, there is a relatively high level of ErbB-4 receptor expression and a moderate level of other EGF-family receptors, whereas MDA-MB-453 cells express low endogenous levels of ErbB-4 and high levels of ErbB-2 and ErbB-3. MDA-MB-231 expresses a high level of EGFR and a relatively low level of ErbB-2, but does not express detectable level of ErbB-3 or ErbB-4. The functional ErbB-4 ribozymes, as well as a control vector, were introduced into these cell lines by stable transfection. The sublines T47D/Rz, MCF-7/Rz, MDA-MB-453/Rz and MDA-MB-231/Rz as well as empty vector control cell lines were established. We then assessed the ribozyme mediated down-regulation of ErbB-4 expression by FACS analysis. FIG. 9 illustrates that ErbB-4 ribozyme capable of down-regulation of endogenous ErbB-4 expression by 50% and 70% in two of the ribozyme transfected T47D pooled population clones, T47D/Rz-poolA and T47D/Rz-pool 20, respectively. We also found that the ErbB-4 expression was almost completely down-regulated in some of the ErbB-4 ribozyme transfected MCF-7 cells, such as MCF-7/RzA4 and MCF-7/RzB1 clones (data not shown), as well as in ribozyme transfected MDA-MB-453 cells (data not shown). However, no effect was observed on other EGF family receptors in these ErbB-4 ribozyme transfected cells, respectively (Data not shown). Furthermore, ribozyme-mediated down-regulation of ErbB-4 receptor expression was confirmed by reduction of ErbB-4 mRNA by Northern blot analysis (data not shown).

EXAMPLE 9

Figure 10:
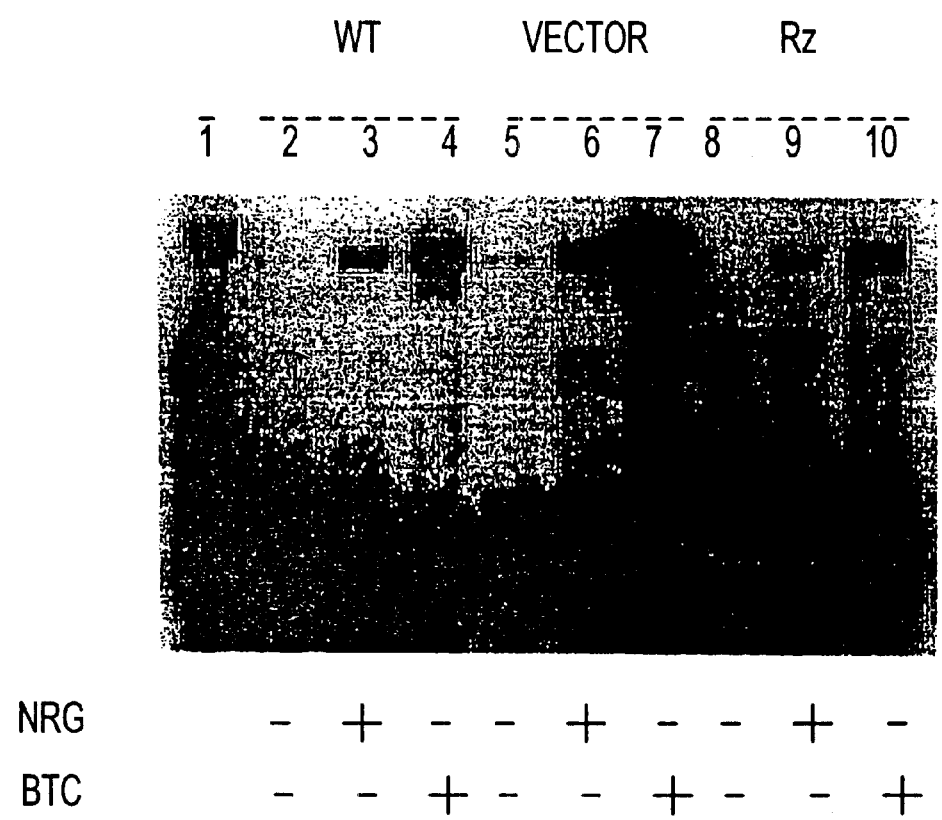
FIG. 10. Reduction of NRG and BTC induced ErbB-4 autophosphorylation in T47D/Rz transfected cells. Cells were treated with or without NRG1-α and BTC (100 ng/ml) for 5 minutes prior to lysis, and 400 ug of lysates were immunoprecipitated with a specific anti-ErbB-4 antibody. Precipitated proteins were then subjected to Western blotting with an anti-phosphotyrosine antibody (UBI). Lane 1: Molecular weight standards. Lane 2,5,8 are untreated samples. Lane 3,6,9 are the lysates from T47D/wt, T47D/Rz cells treated with 100 ng/ml of NRG1-α. Lane 4, 7, 10 are the lysates from T47D/wt, T47D/vector and T47D/Rz cells treated with 100 ng/ml of BTC. Down-regulation of ErbB-4 in T47D cells dramatically reduced NRG and BTC induced ErbB-4.

Reduction of NRG and BTC Induced ErbB-4 Autophosphorylation in T47D/Rz Transfected Cells We next determined whether NRG or BTC-induced ErbB-4 receptor tyrosine phosphorylation was affected by reduction of ErbB-4 expression in ribozyme transfected cells. Phosphorylation experiments were performed on ribozyme transfected clones. FIG. 10 demonstrates that the level of ErbB-4 intrinsic tyrosine kinase activity in T47D/Rz6 Pool 20 transfected cells was markedly reduced when compared with control transfectants (T47D/wt and T47D/Vector) cells. Reduction of phosphorylation correlates with a reduction in ErbB-4 expression level. A similar effect was observed in BTC-induced ErbB-4 tyrosine phosphorylation. These experiments demonstrate that the reduction of ErbB-4 activation correlates with down-regulation of ErbB-4 protein production.

EXAMPLE 10

Figure 11:
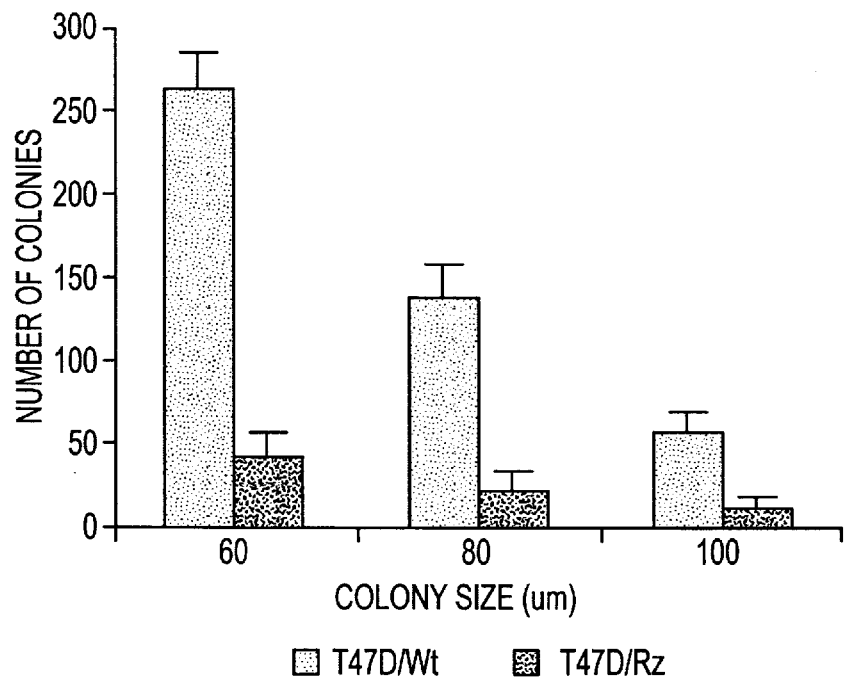
FIG. 11. Growth effects of ErbB-4 ribozyme on T47D cells. Anchorage-independent growth assays: Expression of the ErbB-4 ribozyme in T47D cells inhibits colony formation, independent of colony size. A bottom layer of 0.1 ml IMEM containing 0.6% agar and 10% FCS was prepared in 35 mm tisssue culture dishes. After the bottom layer solidified, cells (10,000 per dish) were than added in a 0.8 ml top layer, containing 0.4% Bacto Agar, and 5% FCS. All samples were prepared in triplicate. The cells were incubated for approximately 12 days at 37° C. Colonies larger than 60 um, 80 um, 100 um, and 120 um were counted by a cell colony counter.
Figure 12:
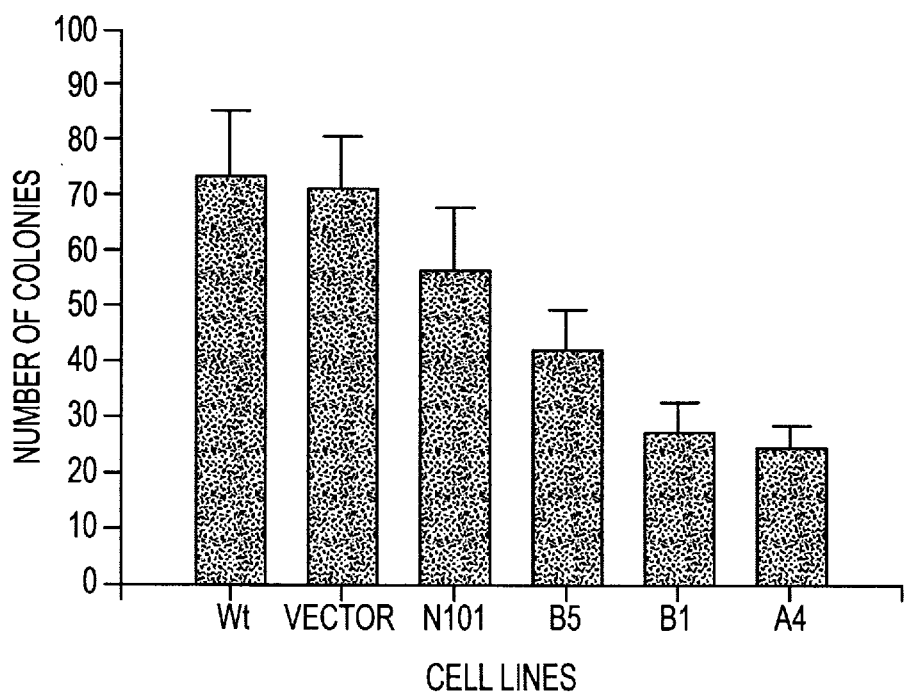
FIG. 12. Growth effects of ErbB-4 ribozyme on MCF-7 cells. Anchorage-independent growth assays: Expression of the ErbB-4 ribozyme in MCF-7 cells inhibits colony formation, independent of colony size. A bottom layer of 0.1 ml IMEM containing 0.6% agar and 10% FCS was prepared in 35 mm tissue culture dishes. After the bottom layer solidified, cells (10,000 per dish) were than added in a 0.8 ml tope layer, containing 0.4% Bacto Agar, and 5% FCS. All samples were prepared in triplicate. The cells were incubated for approximately 12 days at 37° C. Colonies larger than 120 um, 140 um, and 160 um were counted by a cell colony counter.

Down-regulation of ErbB-4 in Cell Lines Expressing Relatively High Level of ErbB-4 Resulted in an Inhibition of Colony Formation In order to assess the biological significance of ErbB-4 in human breast cancer, we evaluated the in vitro growth of ErbB-4 ribozyme transfected T47D, MCF-7, MDA-MB-453 and MDA-MB-231 cells by anchorage-dependent as well as anchorage-independent growth assays. Down-regulation of ErbB-4 expression in cell lines expressing a relatively high level of ErbB-4 (T47D and MCF-7 cells) resulted in an inhibition of colony formation that was independent of colony size. FIG. 11 illustrates that down-regulation of ErbB-4 by 50% in T47D/Rz-poolA cells displayed a 50% reduction in their ability to form colonies in soft agar. Colony formation was almost completely abolished in T47D/Rz-pool20 cells, which had an 80% down-regulation of ErbB-4, indicating a partial reversion of transformation. Furthermore, inhibition of colony formation was independent of threshold colony size. A similar phenotype was observed in ribozyme transfected MCF-7 cells (FIG. 12). These data demonstrated that inhibition of growth is correlated with the level of down-regulation of ErbB-4 in these ribozymes transfected cells. However, growth inhibition was not observed in MDA-MB-453/Rz cells, which express low levels of ErbB-4 and high levels of ErbB-2 and ErbB-3. Interestingly, FACS analysis revealed that the expression of the ErbB-4 receptor was completely abrogated by the ErbB-4 ribozyme in these cells as well (Data not shown). In a parallel experiment, we verified the specificity and efficacy of the anti-ErbB-4 ribozymes with MDA-MB-231 cells, which do not express detectable level of ErbB-4. Obviously, no effect was observed in ribozyme transfected MDA-MB-231 cells, respectively (Data not shown). These data suggest that the biological effect of ErbB-4 receptor expression is dependent upon its relative levels in a given cell line.

EXAMPLE 11

Figure 13:
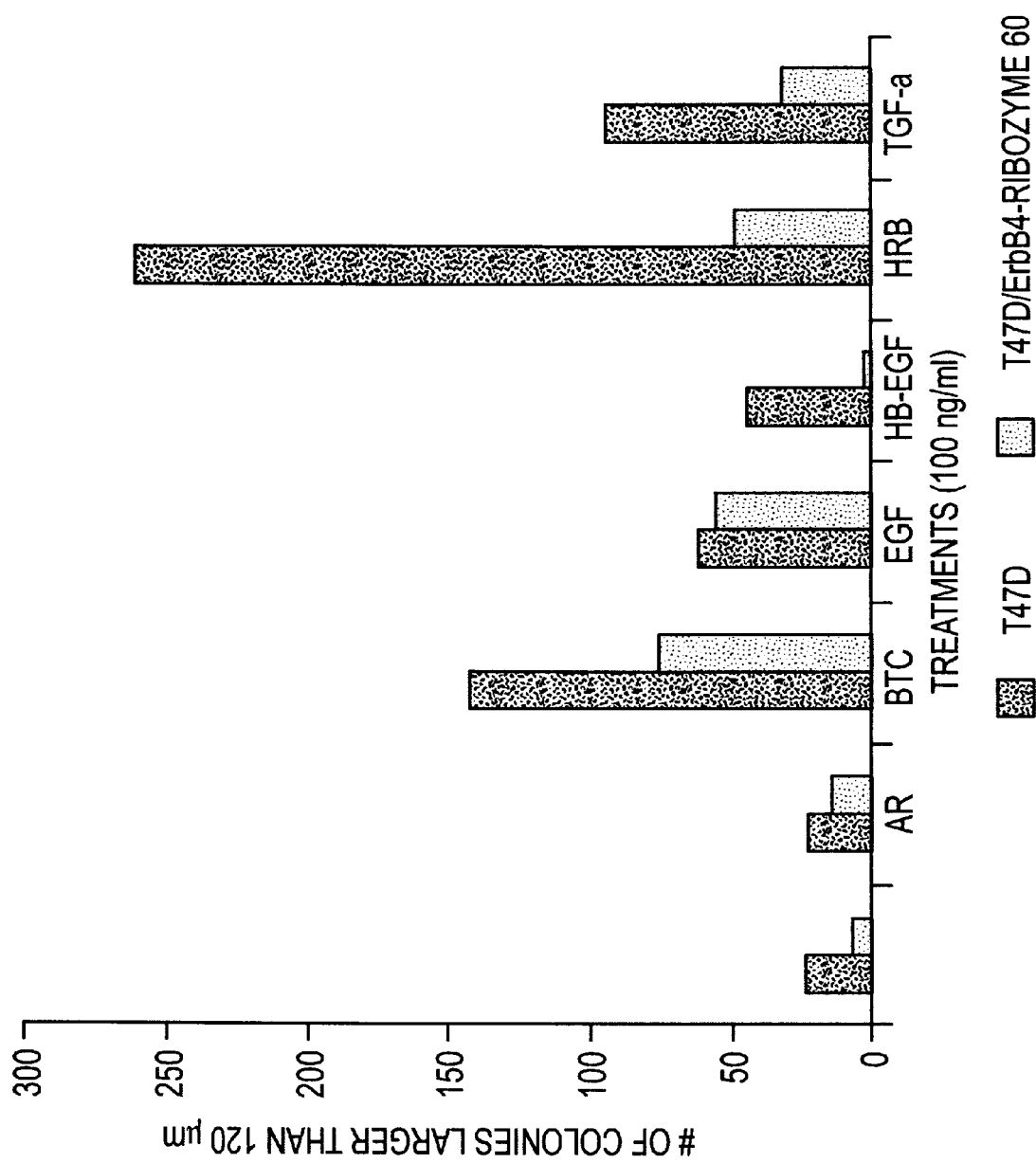
FIG. 13. Down-regulation of endogenous ErbB-4 expression in T47D cells strongly inhibited NRG-induced colony formation. Anchorage-independent growth assays: A bottom layer of 0.1 ml IMEM containing 0.6% agar and 10% FCS was prepared in 35 mm tissue culture dishes. After the bottom layer solidified, cells (10,000 per dish) were than added in a 0.8 ml top layer, containing 0.4% Bacto Agar, and 5% FCS and 100 ng/ml of EGF-like ligands. All samples were prepared in triplicate. The cells were incubated for approximately 15 days at 37° C. Colonies larger than 60 um were counted by a cell colony counter. The blank bars represent the T47D wild type cells. The open bars represent the ErbB-4 ribozyme transfected T47D cells. In the wild type cells, NRG had most effect on a colony formation amount the EGF-like ligands. In ribozyme transfected cells, BTC had the dominant effect and NRG-stimulated colony formation was reduced by 70%.

The Sensitivity of Biological Responses to Different EGF-like Ligands is Dependent upon the Relative Level of ErbB Family Receptors Regulation of ErbB receptor family members activation is very complex. A large number of ErbB ligands have been described (reviewed in Peles and Yarden (1993) BioEssays 15: 815–824; Groenen et al., (1994) Growth Factors 11:235–257; Salomon et al., (1995) Crit. Rev. Oncol.-Hematol. 19: 183–232; Pinkas-Kramarshi et al. (1997) J. Mammary Gland Biol. Neoplasia 2:97–107]. We next compared the effects of EGF-like ligands between ribozyme transfected T47D cells (T47D/Rz) and T47D/wt. We observed that neuregulin induced colony formation was significantly inhibited in T47D/Rz transfected cells. Down-regulation of ErbB-4 in T47D cells reduced NRG stimulated colony formation by 80%. In contrast, wild type T47D cells exhibited an 11-fold increases in colony formation when treated with neuregulin appears to have the most dominant effect among the six of EGF-like ligands. Betacellulin, which predominantly binds to EGFR and can also activate the ErbB-4 and ErbB-2/ErbB-3 heterodimers, had the most dominant effect on the induction of colony formation, when compared with the other EGF-like ligands (FIG. 13). These data demonstrate that NRG was significantly more active than other EGF-like ligands in T47D wild type cells, while down-regulation of ErbB-4 in T47D cells revealed almost complete abrogation of the NRG activity, suggesting that NRG signaling occurs primarily through ErbB-4 in T47D cells. Interestingly, BTC was comparable to NRG stimulating colony formation by nearly six fold in T47D wild type cells and is the dominant ligand in ErbB-4 depleted T47D cells. These results suggested that altering the expression of ErbB-family receptors in the cell results in an alteration in the biological activities of EGF-related peptides.

EXAMPLE 12

Inhibition of Tumor Formation in Nude Mice

Figure 14:
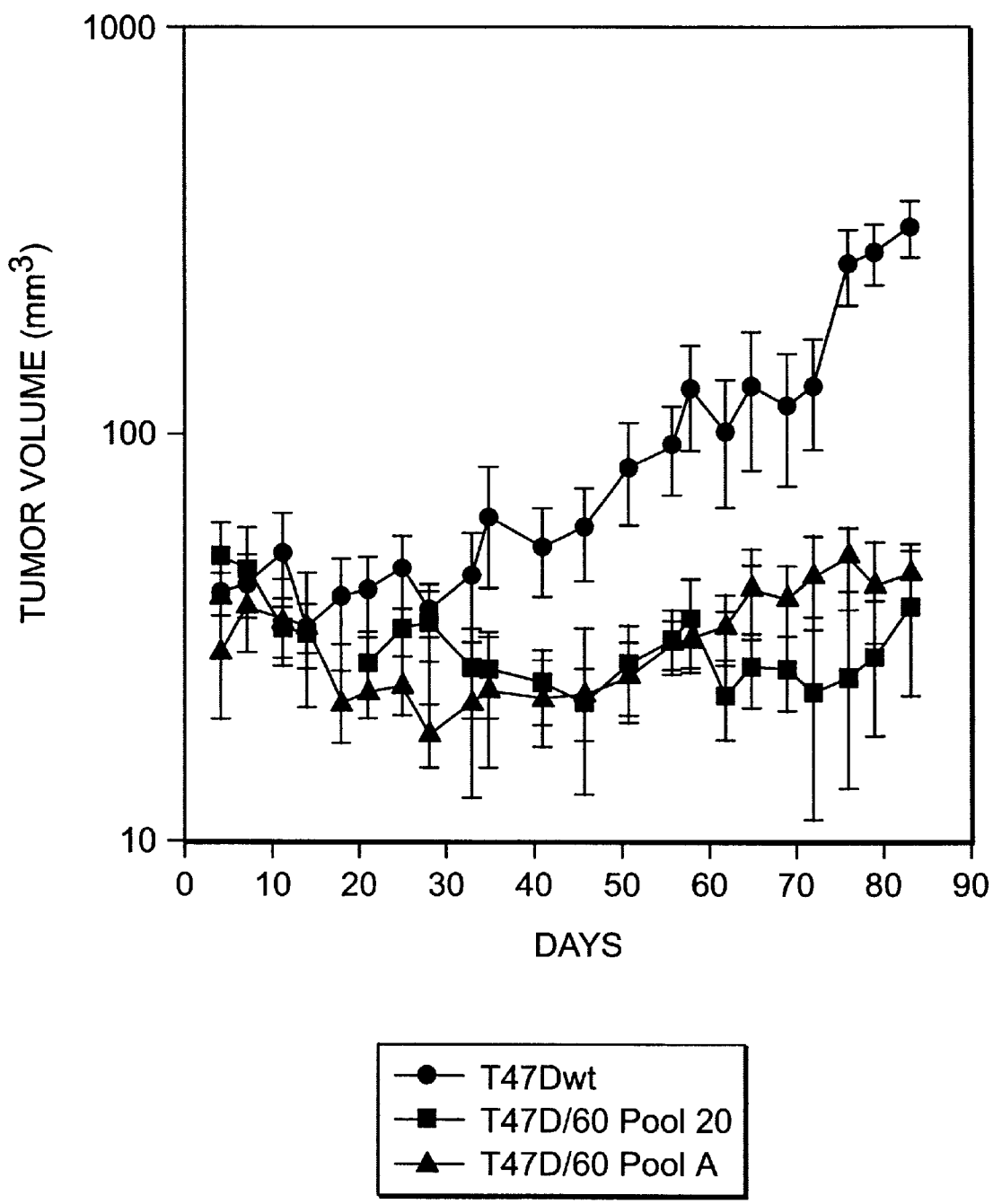
FIG. 14. Growth of T47Dwt and two ErbB-4 ribozyme transfectants in athymic nude mice.
Figure 15:
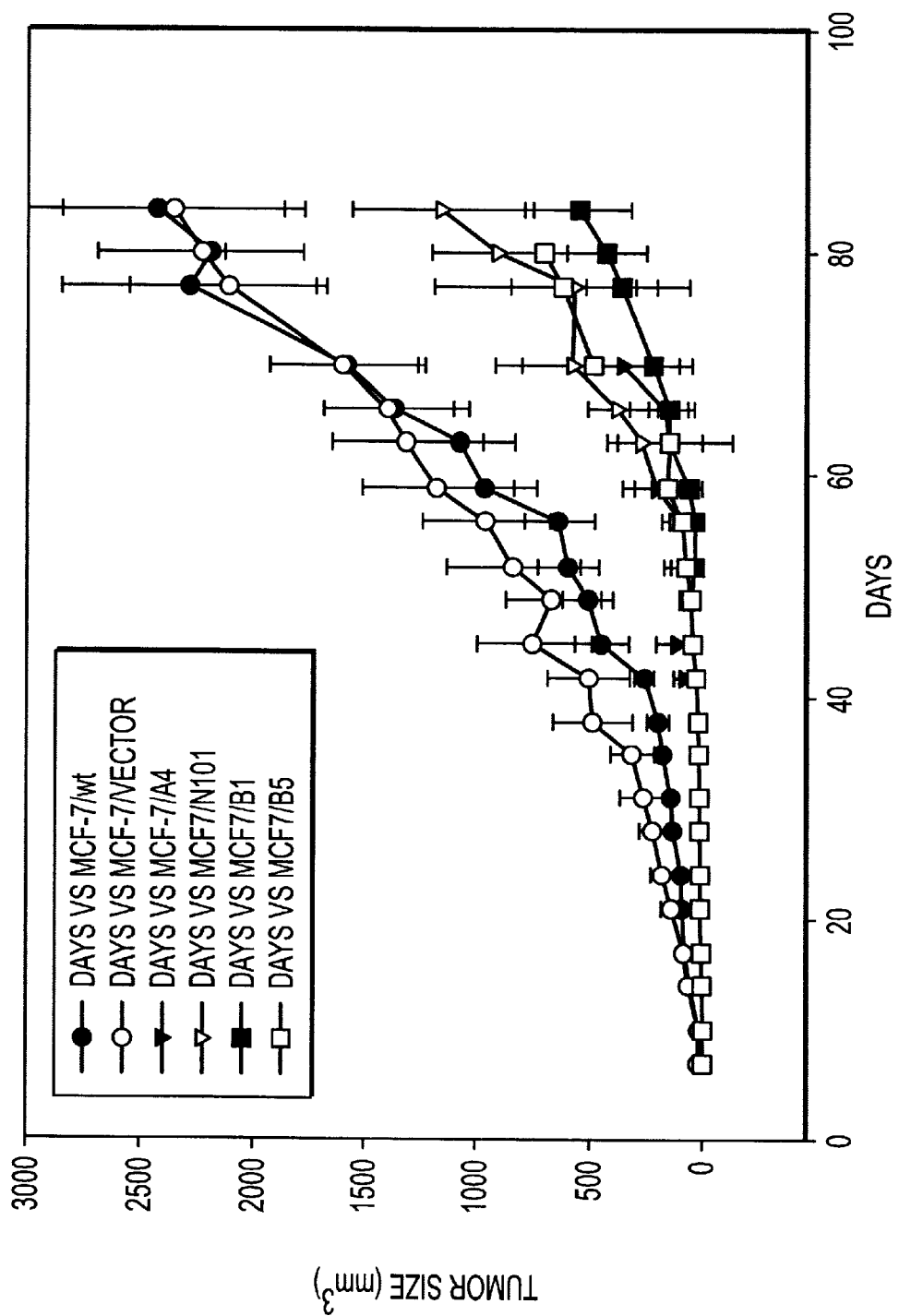
FIG. 15. ErbB-4-ribozyme mediated down-regulation of ErbB-4 in MCF-7 cells resulted in reduction of tumor growth in vivo. $5\times10^6$ MCF-7 wild type cells, as well as the ribozyme transfected cells were implanted in ovariectomized mice. With estradiol treatments, the MCF-7 wild type cells, as well as the empty vector transfected cells grew large tumors to a mean tumor size of 2000±200 mm$^3$ (filled and open circles). In contrast, tumor growth of ribozyme expressing MCF-7 cells was significantly inhibited (p<0.001; student's test) with a mean tumor size of 600±74 mm$^3$(triangles and squares).

Down-regulation of ErbB-4 led to dramatic effects on anchorage-dependent and anchorage-independent growth in MCF-7 and T47D cells. We next explored the in vivo effects of down-regulation of ErbB-4 in MCF-7 and T47D cells. MCF-7 or T47D wild type cells ($5 \times 10^6$) as well as the ribozyme transfected cells were implanted in ovariectomized mice. With estradiol treatments, the T47D wild type cells grew to a mean tumor size of $500 \pm 20$ mm$^3$ (FIG. 14; filled circles). In contrast, tumor growth of ribozyme expressing T47D cells was significantly inhibited (p<0.001; student's t test) with a mean tumor size of $80 \pm 14$ mm$^3$ (FIG. 14; triangles and squares). Moreover, tumor growth of T47D cells transfected with the catalytically inactive ribozyme (Rz21) was not significantly different from control cells (data not shown). Similar experiments were performed with ribozyme transfected MCF-7 cells. FIG. 15 demonstrated that down-regulation of ErbB-4 expression in MCF-7 cells dramatically reduced the tumor formation. With estradiol treatments, the MCF-7 wild type (MCF-7/wt) and an empty vector transfected MCF-7 cells (MCF-7/vector) grew large tumors with a mean tumor size of $2400 \pm 270$ mm$^3$. In contrast, tumor growth of ribozyme expressing MCF-7 cells was drastically inhibited (p<0.0003; student's t test) with a mean tumor size of 580±74 mm$^3$ (p<0.001; student's t test). Table 3 summarizes the in vitro and in vivo effects of down-regulation of ErbB-4 in human breast cancer cell lines.

TABLE 3

Selective growth inhibition with ribozyme-mediated down-regulation of ErbB-4 in breast cancer cells[a]

| Cell line | Expression levels of EGF-family receptors | | | | | Effects of down-regulation of ErbB-4 | |
|---|---|---|---|---|---|---|---|
| | EGFR | ErbB-2 | ErbB-3 | ErbB-4 | ER | % inhibition of colony formation | % inhibition of tumorigenicity |
| MCF-7 | + | ++ | +++ | ++++ | + | 60–80 | 70 |
| T47D | ++ | ++ | +++ | ++++ | + | 50–70 | 50–60 |
| 453 | +/− | ++++ | +++ | − | − | 0 | N/A |
| 231 | ++++ | + | +/− | − | − | 0 | N/A |

453 = MDA-MB-453
231 = MDA-MB-231
The expression levels of ErbB-family receptors were determined by FACS analysis.

EXAMPLE 13

Expression of ErbB-4 in Primary Breast Carcinomas

We next investigated the frequency of ErbB-4 expression in breast carcinomas using immunohistochemical analysis with an anti-ErbB-4 monoclonal antibody. The expression of ErbB-4 was analyzed in 50 primary breast carcinomas. The results showed expression of ErbB-4 in 70% of the total samples (35 of 50) examined. Interestingly, 80%(28 of 35) of the ErbB-4 positive samples were estrogen receptor positive (ER+) breast carcinomas and 67% (10 of 15) of the negative or weak ErbB-4 expressions were estrogen receptor negative (ER−) breast carcinomas (Table 4). It appears that there is a statistically significant (P=0.001) direct correlation between the expression of estrogen receptors and the expression of ErbB-4. We also surveyed the ErbB-4 expression in human breast cancer cell lines by FACS analysis. Surprisingly, most of ER+ cell lines expressed relatively high levels of ErbB-4 and ER− cell lines expressed low levels or non-detectable levels of ErbB-4

TABLE 4

Correlation of ErbB-4 expression with prognostic factors in breast cancer

| ErbB-4 expression | ER | | PR | |
|---|---|---|---|---|
| | − | + | − | + |
| weak/negative (+/−) | 10 | 5 | 9 | 6 |
| positive (++/+++) | 7 | 28 | 9 | 26 |

PR = Progesterone receptor
n = 50

DISCUSSION

In this study, we generated three specific hammerhead ribozymes (Rz) targeted to ErbB-4 mRNA. We have demonstrated that these ErbB-4 ribozymes (Rz6, Rz21, Rz29) effectively catalyze precise cleavage of ErbB-4 mRNA under physiological conditions in an extracellular system (FIG. 2). Furthermore, we demonstrated that these ribozymes do not cleave mRNA of other EGFR family members, despite the high degree of sequence homology shared by these receptors. Point mutation of these ErbB-4 ribozymes in the catalytic domain resulted in loss of catalytic activity and failure to cleave ErbB-4 mRNA. These inactive ribozymes have identical binding arms to the active version but have a mutated catalytic domain. Thus, these mutated versions are capable of binding to the target sequence but are not able to cleave the target mRNA. Taken together, these control experiments demonstrate that the ErbB-4 ribozymes are highly specific for the ErbB-4 mRNA.

Using the 32D cell system to study the intracellular enzymatic activity of ErbB-4 ribozymes, we clearly demonstrated that the ribozymes are specific and effectively downregulate the EGF receptor family members. In this system, one ErbB-4 ribozyme (Rz29) significantly reduced the ErbB-4 mRNA level and down-regulated ErbB-4 receptor expression (FIG. 6), thereby reversing the HRG-induced IL3-independent phenotype of 32D/E4 cells (table 2). Rz6 partially down-regulated the expression of the ErbB-4 receptor, and somewhat blocked the IL3-independent phenotype. In contrast, Rz21 failed to down-regulate the ErbB-4 expression and inhibit the mitogenic response to HRG treatment in 32D/ErbB-4 cells. It is clear from these data that not all of the sites tested are equally amenable to intracellular ribozyme-mediated cleavage. This is in spite of the fact that ribozymes to all of the sites were shown to be catalytically active extracellular biochemical assays. RNA secondary structure or association with cellular proteins may affect target site accessibility. We therefore investigated the specificity and efficacy of these ribozymes in a well-defined cellular system. Two sets of experiments were conducted to control for ribozyme specificity and efficacy intracellularly. Due to the high homology between the EGF receptor family members, the intracellular specificity of ErbB-4 ribozymes was demonstrated using the 32D cells ectopically co-expressing ErbB-2 and ErbB-3. None of the ErbB-4 ribozymes (Rz6, Rz21, Rz29) had any effect on the level of ErbB-2 or ErbB-3 expression or the HRG-induced IL-3-independent phenotype in these 32D derivative cells (Table 2). Moreover, an ErbB-2 ribozyme, previously shown to down-regulate the expression of ErbB-2 mRNA, failed to decrease ErbB-4 expression in 32D/ErbB-4 cells. The lack of down-regulation of ErbB-4 expression in these control experiments is evidence of the high degree of specificity of these ribozymes. Furthermore, in the absence of HRG, cells expressing these ribozymes remained strictly dependent on IL3 for growth. In contrast, two ErbB-4 ribozymes (Rz29 and Rz6) decreased the HRG-induced, IL-3-independent proliferation. Taken together, these phenomena indicate that only the ErbB-4 transcript is directly affected by these ribozymes. Although the ErbB-4 expression was reduced in Rz6- and Rz29-transfected 32D/E4 cells, the remaining ErbB-4 receptors in these cells were still phosphorylated in response to HRG treatment (FIG. 7). This characteristic provides strong support for a cleavage-mediated mechanism of action for the ribozymes. Therefore, the constructed ErbB-4 Rz29 and Rz6 are biologically functional ribozymes and are highly specific for the targeted ErbB-4 mRNA in 32D cells.

To evaluate the effects of down-regulation of ErbB-4 in an ErbB-4-positive human breast cancer line, Rz29 was transfected into T47D cells. Down-regulation of ErbB-4 receptor in T47D cells resulted in reduction of colony formation in anchorage-independent assay and in transfection efficiency compared to vector- or Rz21-transfected cells. The low efficiency of Rz6 and Rz29-expressing, drug-selected clones is unlikely due to a non-specific effects, since all the ribozymes were cloned into the same vector. Furthermore, Rz6 and Rz29 only down-regulated ErbB-4 but not other ErbB-receptor family members. Reduction of colony formation suggests that ErbB-4 expression and mitogenic signaling may be essential for T47D cell survival. Currently, we are conducting these studies using an inducible promoter system. These preliminary findings suggest that down regulation of ErbB-4 expression, as shown by FACS, diminished the ErbB-4-mediated intracellular signaling. Because of heterodimerization between the family receptors, down-regulation of ErbB-4 receptor may also indirectly interrupt receptor signaling pathways initiated by other family members. This could result in diminished tumorigenicity in T47D cells. These results also show that our ribozyme is active in a human carcinoma cell line.

32D cells are strictly dependent upon interleukin-3 (IL-3) for survival and proliferation. However, HRG was capable of stimulating its cognate receptors, coupling to cellular signaling pathways in 32D derivatives and thereby abrogating the IL-3 dependence of these cells. Using the ErbB-4 ribozymes in 32D cell system, we provide the first evidence that the different threshold levels of ErbB-4 expression and activation correlate with different responses to HRG stimulation. High levels of ErbB-4 expression, phosphorylation and homodimerization are necessary for HRG stimulated IL3-independent cell proliferation in the 32D/E4 cells. Low levels of ErbB-4 expression allows HRG-induced phosphorylation, but are insufficient to couple the receptor activation to cellular signaling, particularly in the case of Rz29-transfected 32D/E4 cells. In line with these observations, in a recent study using Ba/F3 cell derivatives, HRG failed to induce the IL-3-independent pathway in the ErbB-4 transfected cells [Riesell, D. J. et al. (1996) Oncogene 12:345–353]. It is possible that the level of ErbB-4 expression in these Ba/F3/ErbB-4 cells is lower than our 32D/E4 cell line. We demonstrate that the IL-3-independent pathway appears to be very sensitive to the amount of ErbB-4 expression, as well as the tyrosine phosphorylation level. The Rz6-transfected cells, whose ErbB-4 expression was down-regulated by 45%, exhibited a weak response to HRG, whereas the Rz29-transfected cells, whose ErbB-4 expression level was down-regulated by 65%, failed to respond HRG stimulation. HRG was still able to induce ErbB-4 receptor phosphorylation in these cells, but the level of phosphorylation was much lower than in the 32/E4 cells. This level of phosphorylation is not sufficient to stimulate the cellular response. These results also suggest that homodimers of ErbB-4 can transmit biological signals. This is consistent with a previous report that ErbB-4 homodimers constitute a functional HRG receptor [Plowman, G. D. et al. (1993) Nature 366:473–475]. HRG can induce 32D/ErbB-2+ErbB-3 cells to bypass the IL3-dependent pathway, presumably due to transphosphorylation and cross talk between the receptors through heterodimerization of ErbB-2 and ErbB-3. These results are consistent with previous studies concerning ErbB receptor transphosphorylation (40). While ErbB-3 appears to be a defective tyrosine kinase receptor, it mediates HRG signals through heterodimer formation with either EGFR or ErbB-2 (Plowman et al., 1993, supra). Furthermore, almost all of the breast cancer cell lines express more than one of the EGFR family members. These results imply that inter-receptor cross-talk may play an important role in human breast cancer.

In this study, we employed ribozyme technology to achieve the functional gene "knockout" strategy to define the role and biological significance of ErbB-4 in human breast cancer. We demonstrated that the ErbB-4 ribozyme is capable of down-regulation of endogenous ErbB-4 expression in several human breast cancer cell lines, but no effect was observed on other members of the EGF receptors family. In stably mass-transfected T47D cells, ErbB-4 ribozyme expression depleted ErbB-4 mRNA and protein levels by 50–75%. This inhibition is even more remarkable when considering that mass-transfected cells (and not clonal subpopulations) were used. This substantial inhibition enabled us to begin a novel study of the effects of a functional ErbB-4 knockout on in vitro and in vivo tumor growth of breast cancer cells. We observed that down-regulation of ErbB-4 in T47D and MCF-7 cells which express relatively high levels of ErbB-4 significantly inhibited colony formation. In addition, down-regulation of ErbB-4 in T47D cells significantly impaired NRG-induced ErbB-4 phosphorylation. However, complete depletion of ErbB-4 did not affect the anchorage-dependent and anchorage-independent growth in MDA-MB-453 cells, which express low levels of endogenous ErbB4 and high levels of ErbB-2 and ErbB-3. Furthermore, down-regulation of ErbB-4 in T47D and MCF-7 cells significantly inhibited tumor formation in athymic nude mice with $P<0.001$, $P<0.0003$. These data provide the first evidence that elevation of ErbB-4 expression plays a proliferation role in vitro and in vivo in some human breast cancer cell lines (T47D, MCF-7). These data suggest that inhibition of growth was observed when over expressed receptors were targeted. Furthermore, ErbB receptors undergo extensive heterodimerization. The inactivation or blocking of ErbB-4 signaling may also disrupt and diminish the EGFR or ErbB-2 signaling pathways, through heterodimerization with ErbB-4. A similar conclusion was reported by Hynes and her colleagues, who found that blocking cell surface expression of ErbB-2 and EGFR by intracellular expression of a single-chain antibody specific for ErbB-2 (scFv-5R) and EGFR (scFv-R1R) led to only a slight reduction in colony formation of T47D cells, which express low levels of ErbB-2 and EGFR. However, in MDA-MB-468 cells, scFv-5R and scFvR1R inhibited colony formation by 90% and 94%, respectively. MDA-MB-468 express high levels of EGFR and TGFα, treatment with a Mab which competes with ligand binding and inhibits cell growth, indicating that these cells are dependent upon an autocrine loop for growth. Despite the fact that these cells have very low levels of ErbB-2, inhibition of colony formation by scFvR suggests that TGFα activated heterodimers of EGFR and ErbB-2 provide the major growth stimulus to these cells [Jannot, C.

B. et al. (1996) *Oncogene* 18:275–282; Beerli, R. R. et al. (1995) *Mol. Cell Biol.* 15:6496–6505]. These data also suggest that depending upon the cellular context, it seems that not only the presence or absence of a specific EGF-family receptor in a given cell line influence the nature of cell proliferation, but also the relative expression level of the ErbB-receptors determines the roles of these receptors in a given cell line. Over expression or a relatively high level of an ErbB-receptor plays a role in breast cancer proliferation. In general, inhibition of growth was observed when over expressed receptors were targeted.

Regulation of ErbB-receptor family members activation is very complex. ErbB receptors undergo extensive heterodimerization which makes ligand-induced signaling even more complex. We show that NRG-stimulated phosphorylation of ErbB-4 was significantly reduced and NRG induced colony formation was substantially reduced from 11 fold to only 2.5 fold in ribozyme transfected T47D cells (T47D/Rz), indicating that the major NRG signaling was through ErbB-4. It implies that NRG signaling through ErbB-2/ErbB-3 heterodimers may play a minor role in T47D cells due to their low expression levels. BTC, a ligand for EGFR, ErbB-4, and also ErbB-2/ErbB-3 heterodimers, exhibited the most dominant effect on induction of colony formation among the EGF-like ligands in T47D/Rz transfectants (FIG. 13). These data indicated that down-regulation of ErbB-4 only partially affects the BTC signaling. Although, BTC signaling through ErbB-4 may be blocked, BTC's may be able to elicit signalling via other ErbB family receptors. These data suggested that altering the expression of ErbB-family receptors in the cell results in altering the biological activities by EGF-related peptides. EGF-related growth factors show distinguishable biological activities, most likely depending on the subsets of ErbB-receptors that become activated.

In addition, we have also investigated the expression of ErbB-4 in primary breast carcinoma, using immunohistochemical analysis with an anti-ErbB-4 monoclonal antibody. ErbB-4 expression was found in 70% of the 50 samples examined. Overexpression of ErbB-4 is correlated with ER+ and progesterone receptor positive (PgR+) primary breast tumors. Although the data are incomplete, a pattern is suggesting that ErbB-4 may be a favorable prognostic factor. It is interesting that overexpression of ErbB-4 is correlated with ER expression, unlike other EGF-family receptors. It will be intriguing to define the mechnism by which ErbB-4 expression maintains ER expression in human breast cancer.

In conclusion, our data suggest that the role and function of EGF-family receptors in breast cancer cells dependent on the relative levels of expression of the EGFR, ErbB-2, and ErbB-4 rather than the absolute levels of any single ErbB family receptors expression.

Our studies provide strong evidence that ribozymes (Rz6, Rz29) specifically target ErbB-4 mRNA for degradation extracellularly and intracellularly. These functional ErbB-4 ribozymes should provide important tools for delineating the biological and biochemical consequences of ErbB-4 expression in human breast cancer cells. Furthermore, our study supports the potential for using ribozymes as therapeutic agents for human breast cancer (Gassmann, M et al. (1995) Nature 378: 390–394; Lieber, A. et al. (1996) J. Virol. 70:8782–8791; Grassi, G. and Marini, J. C. (1996) Ann. Med. (England) 28: 499–510; Birikh, K. R. et al. (1997) Eur. J. Biochem 245:1–16; Prislei, S. et al. (1997) RNA 3: 677–687).

What is claimed is:

1. An enzymatic RNA molecule which specifically cleaves mRNA produced from the gene ErbB-4, wherein the enzymatic RNA molecule specifically cleaves RNA sequence consisting of any of SEQ ID NOs 1–3, and wherein said enzymatic RNA is in a hammerhead motif.

2. An enzymatic RNA molecule which specifically cleaves mRNA produced from the gene ErbB-4, wherein the enzymatic RNA molecule specifically cleaves RNA sequence consisting of any of SEQ ID NOs 1–3, and wherein said enzymatic RNA is in a hammerhead motif and consisting of any sequence selected from the group consisting of SEQ ID NOs 4–6.

* * * * *

UNITED STATES PATENT AND TRADEMARK OFFICE
CERTIFICATE OF CORRECTION

PATENT NO. : 6,566,104 B1
DATED : May 20, 2003
INVENTOR(S) : Tang et al.

It is certified that error appears in the above-identified patent and that said Letters Patent is hereby corrected as shown below:

Column 1,
Line 9, insert:
-- U.S. GOVERNMENT RIGHTS
The U.S. Government may have certain rights in the present invention pursuant to the United States Department of the Army Grant No. DAMD17-96-1-6031. --.

Signed and Sealed this

Twenty-fourth Day of January, 2006

JON W. DUDAS
*Director of the United States Patent and Trademark Office*